(12) United States Patent
Bertozzi et al.

(10) Patent No.: US 7,589,182 B1
(45) Date of Patent: Sep. 15, 2009

(54) ANTI-SULFOTYROSINE ANTIBODIES

(75) Inventors: Carolyn R. Bertozzi, Berkeley, CA (US); John Kehoe, Saint Davids, PA (US); Andrew M. Bradbury, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/900,689

(22) Filed: Sep. 12, 2007

Related U.S. Application Data

(63) Continuation-in-part of application No. 11/328,899, filed on Jan. 9, 2006, now abandoned.

(60) Provisional application No. 60/642,445, filed on Jan. 7, 2005.

(51) Int. Cl.
C07K 16/00 (2006.01)
C07K 16/46 (2006.01)
A61K 39/395 (2006.01)

(52) U.S. Cl. .............. 530/388.25; 530/387.1; 530/387.3; 530/388.1; 530/388.15; 424/130.1; 424/135.1; 424/141.1; 424/145.1

(58) Field of Classification Search .......... None
See application file for complete search history.

(56) References Cited

U.S. PATENT DOCUMENTS

2004/0002450 A1* 1/2004 Lazarovits et al. .......... 514/12

FOREIGN PATENT DOCUMENTS

| EP | 0481790 | 2/1999 |
|---|---|---|
| WO | WO9401523 | 5/1994 |
| WO | WO9709351 | 3/1997 |

OTHER PUBLICATIONS

Lederman et al. Molecular Immunology 28: 1171-1181, 1991.*
Li et al. PNAS 77: 3211-3214, 1980.*
Rudikoff et al. PNAS 1982 79:1979.*
Huttner, 1998, Ann. Rev. Physiol. 50:363-376.
Bundgaard et al., 2002, Methods in Molecular Biology: Post-translational Modification of Proteins, pp. 223-239.
Snapp et al., 1998, Blood 91:154-164.
Persic et al., 1997, Gene 187:9-18.
Kehoe, J.N., *New Tools for Studying Tyrosine Sulfation*, PhD Thesis, Univ. California, Berkeley 2004.
Sblattero and Bradbury, 2000, Nature Biotechnology 18:75-80.

* cited by examiner

*Primary Examiner*—Phillip Gambel
*Assistant Examiner*—Sharon Wen
(74) *Attorney, Agent, or Firm*—Kenneth K. Sharples

(57) ABSTRACT

The invention provides anti-sulfotyrosine specific antibodies capable of detecting and isolating polypeptides that are tyrosine-sulfated. The sulfotyrosine antibodies and antibody fragments of the invention may be used to discriminate between the non-sulfated and sulfated forms of such proteins, using any number of immunological assays, such ELISAs, immunoblots, Western Blots, immunoprecipitations, and the like. Using a phage-display system, single chain antibodies (scFvs) were generated and screened against tyrosine-sulfated synthetic peptide antigens, resulting in the isolation of scFvs that specifically recognize sulfotyrosine-containing peptides and/or demonstrate sulfotyrosine-specific binding in tyrosine sulfated proteins. The VH and VL genes from one such sulfotyrosine-specific scFv were employed to generate a full length, sulfotyrosine-specific immunoglobulin.

13 Claims, 8 Drawing Sheets

FIG. 1

B
Pep1   H$_2$N-KDKKYATE<u>Y</u>EYLDYDFC-COOH
Pep1S  H$_2$N-KDKKYATEYEYLDYDFC-COOH
                     |
                   SO$_3^-$
Pep2   H$_2$N-KAKISDPD<u>Y</u>MTGYMDAC-COOH
Pep2S  H$_2$N-KAKISDPDYMTGYMDAC-COOH
                     |
                   SO$_3^-$

D
Fibrinogen    VSVEHEVDVEY<u>P</u>-COOH
IgM           LEGSDE<u>Y</u>LVCKIH
Thyroglobulin H$_2$N-DIPE<u>Y</u>QV
Hirudin       GDFEEIPEE<u>Y</u>LQ-COOH
Vitronectin   PEDE<u>Y</u>TV<u>Y</u>DDGEEKNNA
C4            MEANED<u>Y</u>ED<u>Y</u>EYDELPAK

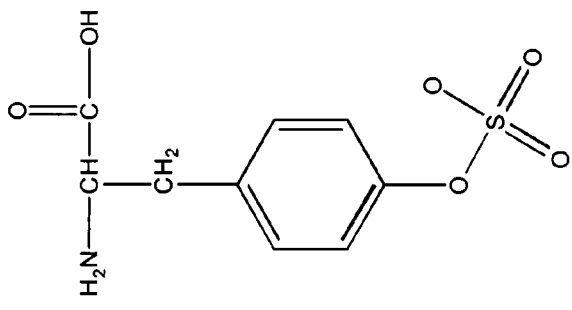

A

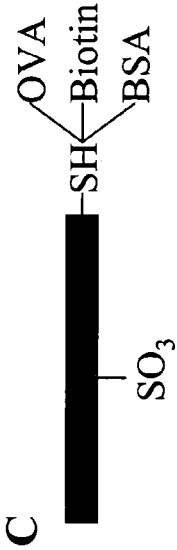

C

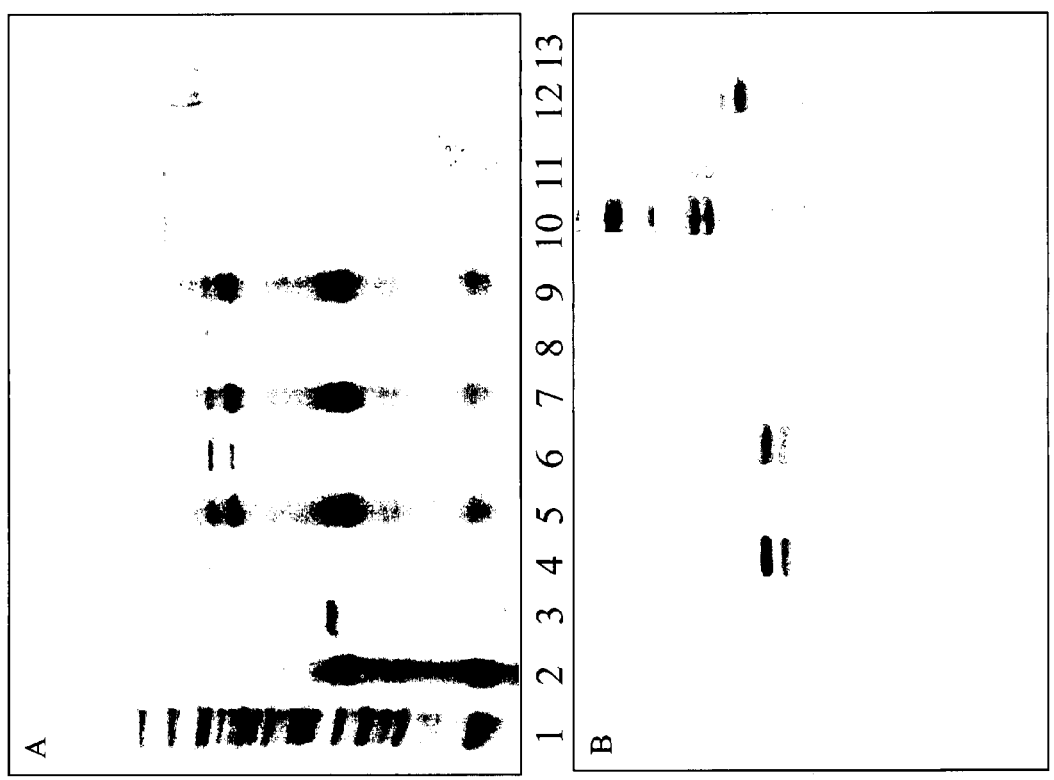

ANTI-SULFOTYROSINE ANTIBODIES

RELATED APPLICATIONS

This patent application is a continuation-in-part of, and claims priority under 35 USC 120 to, U.S. patent application Ser. No. 11/328,899, filed Jan. 9, 2006, now abandoned which claims priority under 35 USC 119 to U.S. Provisional patent application No. 60/642,445, filed Jan. 7, 2005, the entire disclosures of which are hereby incorporated by reference.

STATEMENT AS TO RIGHTS TO INVENTIONS MADE UNDER FEDERALLY SPONSORED RESEARCH OR DEVELOPMENT

This invention was made with government support under Contract No. W-7405-ENG-36 awarded by the United States Department of Energy to The Regents of The University of California. The government has certain rights in this invention.

BACKGROUND OF THE INVENTION

Tyrosine sulfation is an ubiquitous post-translational modification that occurs in essentially all animal cells containing a Golgi apparatus (Huttner, 1998, Ann. Rev. Physiol. 50: 363-376). As much as 1% of the tyrosine residues in an organisms total protein are capable of being sulfated. Tyrosine sulfation of proteins occurs in the trans-Golgi, and the modification appears to be involved in intracellular transport, proteolytic processing and alteration of biological activity. The ability to detect, isolate and differentiate sulfotyrosine-containing proteins would therefore prove extremely valuable. However, no antibody capable of discriminating tyrosine-sulfated proteins from non-sulfated proteins has been described. More particularly, tyrosine sulfation has been found to drive extracellular protein-protein interactions. The archetypal example is the interaction between PSGL-1 and P-selectin, in which PSGL-1's sulfated tyrosine residues are positioned to form hydrogen bonds with P-selectin. Additionally, the tyrosine-sulfated chemokine receptors CCR5, CXCR4, and CCR2 rely on their sulfate groups to increase binding affinity for their chemokines, and in the case of CCR5 are exploited by HIV to mediate infection.

Antibodies against posttranslational modifications have proven to be vital tools for functional studies. For example, an antibody against nitrotyrosine was recently used to identify proteins which are nitrated during the inflammatory response, and antibodies against tyrosine phosphate have been widely used for decades. The obvious utility of an antibody against tyrosine sulfate has led a number of laboratories to pursue this important tool (Bundgaard et al., 2002, *Analysis of Tyrosine-O-Sulfation*, Methods in Molecular Biology Posttranslational Modification of Proteins, pp. 223-239). While an antibody whose binding epitope includes tyrosine sulfate has been reported (Snapp et al., 1998, Blood 91: 154-164), there are no reports of an antibody that recognizes only a sulfated tyrosine residue, despite numerous unsuccessful immunization attempts to derive antibodies recognizing sulfated tyrosines. One explanation for these failures is that the presence of sulfated tyrosine residues in many secreted and membrane-bound proteins has led vertebrate immune systems to become tolerant of the modification, rendering standard immunization-based antibody generation methodologies useless.

One way to overcome the limitations of intact immune systems in the generation of specific antibodies against non-immunogenic targets is to use phage antibody libraries rather than immunization. In this technique large numbers ($\geq 10^9$) of different antibodies are displayed on the surface of filamentous phage and specific binders are selected on the basis of their binding abilities to target antigens. The fact that this technology is completely in vitro, using either natural rearranged or synthetic V genes, overcomes the intrinsic biases of the immune system. Although phage antibodies have been selected against large numbers of different polypeptide and chemical targets, including specific peptides, there have been no descriptions of the use of this technology to select antibodies against post-translational modifications.

There is therefore a need for antibodies capable of specifically recognizing tyrosine-sulfated proteins and capable of distinguishing between sulfated and non-sulfated proteins. The present invention addresses this need.

SUMMARY OF THE INVENTION

The invention provides anti-sulfotyrosine specific antibodies, antibody fragments, and immunological methods capable of detecting and isolating polypeptides that are tyrosine-sulfated. Polynucleotides encoding the sulfotyrosine antibodies and antibody fragments, vectors and expression vectors comprising such polynucleotides, and host cells used for the production of the antibodies and antibody fragments of the invention are also provided. Further, methods of detecting, isolating, and quantifying sulfotyrosine-containing proteins are provided. The sulfotyrosine antibodies and antibody fragments of the invention may be used to discriminate between the non-sulfated and sulfated forms of such proteins. Preferred sulfotyrosine antibodies and sulfotyrosine antibody fragments of the invention specifically bind to a polypeptide containing a sulfated tyrosine, but do not bind or weakly bind to a polypeptide that does not contain a sulfated tyrosine, in standard immunological detection assays, including without limitation, ELISA, immunoblot, Western Blot, immunoprecipitation, and the like, under conditions typically employed for such assays.

Using a phage-display system, single chain antibodies (scFvs) were generated and screened against tyrosine-sulfated synthetic peptide antigens, resulting in the isolation of scFvs that specifically recognize sulfotyrosine-containing peptides and/or demonstrate sulfotyrosine-specific binding in tyrosine sulfated proteins (see Examples 1 and 2, infra). The single chain antibodies provided herein may be multimerized or cloned into various immunoglobulin scaffolds and expressed as full length antibodies, as is generally known. In an exemplified embodiment, a sulfotyrosine-specific IgG was generated using the VH and VL genes of a sulfotyrosine-specific scFv (see Examples 3 and 4, infra).

The sulfotyrosine antibodies and antibody fragments of the invention will be useful in a wide variety of immunological protein assays and isolation procedures, including without limitation, ELISAs, Western Blots and other immunoblot techniques, immunohistochemical assays, various affinity purification methods, and the like, and may be used in proteomics-based approaches to the identification and isolation of tyrosine-sulfated proteins, in cell-based assays of inhibitor candidates, and in drug-screening and development endeavors, among other uses.

BRIEF DESCRIPTION OF THE DRAWINGS

FIG. 1. (A): structure of the tyrosine sulfate post-translational modification. (B): sequences of the two peptides used for selection; the tyrosine which is sulfated is indicated in bold, with the $SO_3$ attached. (C): Each of the peptides was coupled to ovalbumin, BSA or biotin via the C terminal SH group. (D): amino acid sequences flanking known tyrosine sulfate modification sites.

FIG. 8. (A): Polyacrylamide gel electrophoresis of different proteins treated (lanes 5, 7, 9, 11 and 13), and not (lanes 1, 4, 6, 8, 10 and 12), with abalone sulfatase. (B): the same proteins as in (A) analyzed by Western Blotting using the IgG (lanes 1-11) or scFv-AP fusion (12 and 13). Lanes 1) *E. coli* extract; 2) abalone sulfatase; 3) Markers; 4 & 5) Fibrinogen 1S; 6 & 7) Fibrinogen IV; 8 & 9) Rat fibrinogen; 10 & 11) human C4; 12 & 13) vitronectin.

DETAILED DESCRIPTION OF THE INVENTION

Figure 2:
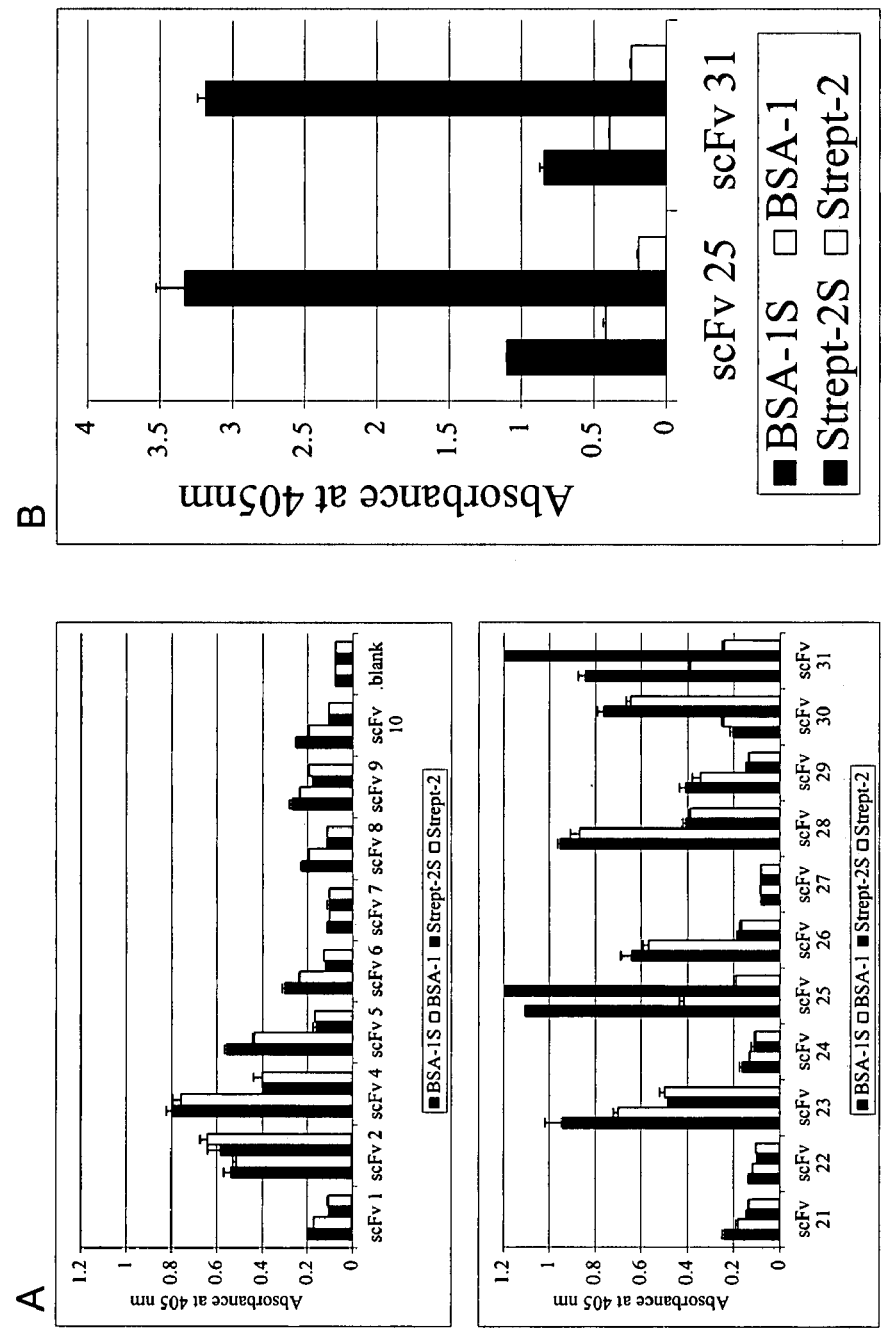
FIG. 2. Binding capabilities of scFvs. (A): soluble scFv ELISA results for 22 of the putatively positive clones identified by phage ELISA. (B): confirmatory ELISA with the two clones scFv25 and 32 identified as binding in a sulfate dependent manner. BSA-1S and BSA-1 represent peptide 1 coupled to BSA in the sulfated and non-sulfated forms.

The invention provides antibodies, antibody fragments, and immunological methods capable of detecting and isolating polypeptides that are tyrosine-sulfated. Polynucleotides encoding the sulfotyrosine antibodies and antibody fragments, vectors and expression vectors comprising such polynucleotides, and host cells used for the production of the antibodies and antibody fragments of the invention are also provided. Further, methods of detecting, isolating, and quantifying sulfotyrosine-containing proteins are provided. The sulfotyrosine antibodies and antibody fragments of the invention may be used to discriminate between the non-sulfated and sulfated forms of such proteins. Preferred sulfotyrosine antibodies and sulfotyrosine antibody fragments of the invention specifically bind to a polypeptide containing a sulfated tyrosine, but do not bind or weakly bind to a polypeptide that does not contain a sulfated tyrosine, in standard immunological detection assays, including without limitation, ELISA, immunoblot, Western Blot, immunoprecipitation, and the like, under conditions typically employed for such assays.

To date, no antibody or other tool capable of specifically identifying proteins containing sulfated tyrosine has been described, representing a fundamental obstacle in the study of this important post-translational modification. The present invention provides antibodies which specifically recognize and bind sulfotyrosine residues in both synthetic peptides and sulfated proteins, but which do not bind to the unsulfated counterpart peptides or de-sulfated counterpart proteins.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The terms "antibody" and "immunoglobulin" are used interchangeably in the broadest sense and includes monoclonal antibodies, polyclonal antibodies, multivalent antibodies, and multi specific antibodies (e.g., bispecific antibodies so long as they exhibit the desired biological activity), regardless of how they are produced (i.e., using immunization, recombinant, synthetic methodologies).

The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "$V_L$" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment.

The terms "anti-sulfotyrosine antibody" and "sulfotyrosine antibody" are used interchangeably and refer to antibodies that are specific for and bind specifically to a sulfated tyrosine antigenic determinant in a sulfotyrosine-containing polypeptide.

A "sulfated tyrosine antigenic determinant" may be an antigenic determinant located entirely within the sulfated tyrosine residue, or may comprise the sulfated tyrosine residue and at least a part of one or more amino acid residues within the polypeptide.

As used herein, the terms "specific", "specifically reactive", "specific binding", "specifically binds" and "binds specifically" when used in connection with the antibodies and antibody fragments of the invention refer to the selective binding of sulfotyrosine antibodies and sulfotyrosine antibody fragments to a sulfated tyrosine antigenic determinant in a polypeptide, generally as determined using standard immunological detection assays, including without limitation ELISA, immunoblot, Western Blot, immunohistochemical and immunoprecipitation assays, under conditions typically employed for conducting such assays, but are not bind or bind weakly to polypeptides that do not contain a sulfated tyrosine. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity).

Antibodies and antibody fragments may be tested for such specificity using methods well know in the art and as described herein. For example, in general, specificity may be established by comparing binding to appropriate (sulfotyrosine) antigen with binding to an irrelevant antigen or antigen mixture under a given set of conditions. As used herein, a "sulfotyrosine antigen" is a peptide or polypeptide that includes a sulfated tyrosine residue. If the antibody binds to the sulfotyrosine antigen at least two times more (or, two times as strongly) than to irrelevant antigen or antigen mixture, then it is considered to be specific. In one embodiment, sulfotyrosine antigen is a synthetic peptide containing at least one sulfated tyrosine residue, and the irrelevant antigen is a synthetic peptide which is identical except that the tyrosine residue(s) is (are) not sulfated. Two such pairs of peptides which differ only in respect of the sulfation state of the tyrosine residue contained therein (i.e., either sulfated or not sulfated) are provided herein, see Example 1, infra, and SEQ ID NOS: 9-12. In another embodiment, sulfotyrosine antigen is a protein containing a sulfated tyrosine residue, and the irrelevant antigen is the same protein which has been treated to remove sulfate from the tyrosine residue (i.e., using a sulfatase enzyme). Examples of such proteins include without limitation IgM, thyroglobin, and fibrinogen. Additional proteins which may used to define specificity include sulfotyrosine containing proteins which bind specifically to scFv 25 as provided infra (using enzymatically de-sulfated protein as the irrelevant antigen). Further, irrelevant antigens may comprise polypeptides containing a phosphated and/or nitrosylated tyrosine residue(s) but not a sulfated tyrosine residue. Preferred sulfotyrosine antibodies of the invention are those which demonstrate specificity to at least two different sulfotyrosine antigens.

The terms "sulfotyrosine", "tyrosine sulfate" and "sulfated tyrosine" are used interchangeably and refer to O-sulfate modified tyrosine.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2; and etc. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not as antibody fragments as defined below. The terms particularly refer to an antibody with heavy chains that contain the Fc region. A full length antibody can be a native sequence antibody or an antibody variant.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd, segments (VH—CH1-VH—CH1) which, together with complementary light chain polypeptides, form a pair of antigen binding regions.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain.

As used herein, the term "single-chain Fv" or "scFv" or "single chain" antibody refers to antibody fragments comprising the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

The terms "anti-sulfotyrosine antibody fragment" and "sulfotyrosine antibody fragment" are used interchangeably and refer to antibody fragments that specifically bind to a sulfated tyrosine antigenic determinant in a polypeptide. The terms "anti-sulfotyrosine scFv", anti-sulfotyrosine single chain antibody", "sulfotyrosine scFv", and "sulfotyrosine single chain antibody" are used interchangeably and refer to single chain antibodies that specifically bind to a sulfated tyrosine, antigenic determinant in a polypeptide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. The monoclonal antibodies of the invention may be generated by recombinant DNA methods, and are sometimes referred to as "recombinant antibodies" or "recombinant monoclonal antibodies" herein.

Recombinant antibody fragments may be isolated from phage antibody libraries using techniques well known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

An "affinity matured" antibody is one with one or more modifications (mutations) in one or more CDRs thereof which result in an improvement in the affinity of the antibody for antigen, compared to the unmodified parent antibody. Preferred affinity matured antibodies will have nanomolar or even picomolar affinities for the target antigen. Affinity matured antibodies are produced by various procedures known in the art, including by variable domain shuffling (see, e.g., Marks et al. 1992, Bio/Technology 10:779-783), random mutagenesis of CDR and/or framework residues (see, e.g., Barbas et al., 1994, Proc Nat. Acad. Sci, USA 91:3809-3813; Schier et al., 1995, Gene 169:147-155; Yelton et al., 1995, J. Immunol. 155:1994-2004; Jackson et al., 1995, J. Immunol. 154(7):3310-9; and, Hawkins et al, 1992, J. Mol. Biol. 226: 889-896).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "vector" refers to a nucleic acid molecule capable of transporting another nucleic acid to which it has been linked. For example, one type of vector is a plasmid, a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" or "expression vectors".

The term "host cell" (or "recombinant host cell"), as used herein, refers to a cell that has been genetically altered, or is capable of being genetically altered by introduction of an exogenous polynucleotide, such as a recombinant plasmid or vector, and includes not only the particular subject cell but also the progeny thereof. Because certain modifications may occur in succeeding generations due to either mutation or environmental influences, such progeny may not, in fact, be identical to the parent cell, but are still included within the scope of the term "host cell" as used herein.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as VH and VL genes or polypeptides (i.e., in a scFv), and serves to place the two molecules in a preferred configuration.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "label" and "detectable label" refer to a detectable compound or composition which is conjugated directly or indirectly to the antibody so as to generate a "labeled" or "detectably labeled" antibody. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, $M=5$, $N=-4$ and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

A "display vector" refers to a vector used to create a cell or virus that displays, i.e., expresses a display protein comprising a heterologous polypeptide, on its surface or in a cell compartment such that the polypeptide is accessible to test binding to target molecules of interest, such as antigens.

A "display library" refers to a population of display vehicles, often, but not always, cells or viruses. The "display vehicle" provides both the nucleic acid encoding a peptide as well as the peptide, such that the peptide is available for binding to a target molecule and further, provides a link between the peptide and the nucleic acid sequence that encodes the peptide. Various "display libraries" are known to those of skill in the art and include libraries such as phage, phagemids, yeast and other eukaryotic cells, bacterial display libraries, plasmid display libraries as well as in vitro libraries that do not require cells, for example ribosome display libraries or mRNA display libraries, where a physical linkage occurs between the mRNA or cDNA nucleic acid, and the protein encoded by the mRNA or cDNA.

A "phage expression vector" or "phagemid" refers to any phage-based recombinant expression system for the purpose of expressing a nucleic acid sequence in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is "in phase" the protein it encodes will be expressed as part of the coat protein. Thus, libraries of nucleic acid sequences, such as a genomic library from a specific cell or chromosome, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn, 1996 Curr. Opin. Biotechnol. 7:547-553). See, e.g., description of phage display libraries, below.

The term "amplification" means that the number of copies of a polynucleotide is increased.

PREFERRED EMBODIMENTS

In one aspect, the invention relates to sulfotyrosine antibodies. The sulfotyrosine antibodies of the invention are specific for a sulfated tyrosine antigenic determinant in a sulfotyrosine-containing polypeptide. Sulfotyrosine antibodies may be polyclonal, monoclonal, and may be produced by recombinant means or in cells derived from immunizations. Preferred sulfotyrosine antibodies are isolated, purified or semi-purified such that they retain specificity in the desired application. In one embodiment, a sulfotyrosine antibody of the invention comprises a heavy chain variable region having an amino acid sequence that is at least 80%, preferably about 90%, 91%, 92%, 93% or 94%, and most preferably about 95% or more, identical to the amino acid sequence of SEQ ID NO: 8. In another embodiment, a sulfotyrosine antibody of the invention comprises a light chain variable region having an amino acid sequence that is at least 80%, preferably about 90%, 91%, 92%, 93% or 94%, and most preferably about 95% or more, identical to the amino acid sequence of SEQ ID NO: 4. Yet another embodiment is a sulfotyrosine antibody comprising a heavy chain variable region having an amino acid sequence that is at least 80%, preferably about 90%, 91%, 92%, 93% or 94%, and most preferably about 95% or more, identical to the amino acid sequence of SEQ ID NO: 8, and a light chain variable region an amino acid sequence that is at least 80%, preferably about 90%, 91%, 92%, 93% or 94%, and most preferably about 95% or more, identical to the amino acid sequence of SEQ ID NO: 4. In another embodiment, a sulfotyrosine antibody comprises a heavy chain variable region having the amino acid sequence of SEQ ID NO: 8, and a light chain variable region having the amino acid sequence of SEQ ID NO: 4. The sulfotyrosine antibodies of the invention may be of the immunoglobulin classes IgA, IgD, IgE, IgG and IgM and subclasses thereof.

A related aspect of the invention relates to sulfotyrosine antibody fragments. The sulfotyrosine antibody fragments of the invention are specific for a sulfated tyrosine antigenic determinant in a sulfotyrosine-containing polypeptide. Such fragments may be generated from intact antibodies or through the use of recombinant technology. For example, in one embodiment, a recombinant sulfotyrosine antibody fragment is a single chain antibody or scFv. In a related embodiment, a recombinant sulfotyrosine antibody fragment is a single chain an Fab or Fab' fragment. Such recombinant sulfotyrosine antibody fragments may comprise a heavy chain variable region having an amino acid sequence that is at least 80%, preferably about 90%, 91%, 92%, 93% or 94%, and most preferably about 95% or more, identical to the amino acid sequence of SEQ ID NO: 8. In another embodiment, a recombinant sulfotyrosine antibody fragment comprises a light chain variable region having an amino acid sequence that is at least 80%, preferably about 90%, 91%, 92%, 93% or 94%, and most preferably about 95% or more, identical to the amino acid sequence of SEQ ID NO: 4. Yet another embodiment is a recombinant sulfotyrosine antibody fragment comprising a heavy chain variable region having an amino acid sequence that is at least 80%, preferably about 90%, 91%, 92%, 93% or 94%, and most preferably about 95% or more, identical to the amino acid sequence of SEQ ID NO: 8, and a light chain variable region an amino acid sequence that is at least 80%, preferably about 90%, 91%, 92%, 93% or 94%, and most preferably about 95% or more, identical to the amino acid sequence of SEQ ID NO: 4.

The sulfotyrosine antibodies and antibody fragments of the invention may be detectably labeled as is generally known. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

Sulfotyrosine-specific scFvs may be isolated using selection and screening strategies which utilize sulfotyrosine antigens. A number of selection and screening strategies may be adopted for isolating single chain sulfotyrosine antibody fragments. Diversity libraries may, for example, be generated using phage display or other display methods. In one embodiment, one or more pairs of such sulfotyrosine antigens are employed, in combination with paired "irrelevant" antigens. Examples of such sulfotyrosine and irrelevant antigens include but are not limited to the peptides of SEQ ID NOS: 9-12. Exemplary selection and screening strategies are described in the Examples, infra.

As further described in Example 1, infra, libraries of phage-displayed single chain variable fragments (scFvs) containing natural combinations of heavy and light chain variable regions were used to select scFvs recognizing tyrosine sulfate. As illustrated in the Examples, several scFvs which bind specifically or preferentially to synthetic peptides containing a sulfated tyrosine were isolated and studied. For example, clone scFv 25 appears to be highly specific for the sulfotyrosine modification in both the synthetic peptides and in tyrosine-sulfated proteins.

Construction of phage display libraries exploits the bacteriophage's ability to display peptides and proteins on their surfaces, i.e., on their capsids. Often, filamentous phage such as M13, fd, or f1 are used. Filamentous phage contain single-stranded DNA surrounded by multiple copies of genes encoding major and minor coat proteins, e.g., pIII. Coat proteins are displayed on the capsid's outer surface. DNA sequences inserted in-frame with capsid protein genes are co-transcribed to generate fusion proteins or protein fragments displayed on the phage surface. Phage libraries thus can display peptides representative of the diversity of the inserted sequences. Significantly, these peptides can be displayed in "natural" folded conformations. The fluorescent binding ligands expressed on phage display libraries can then bind target molecules, i.e., they can specifically interact with binding partner molecules such as antigens, e.g., (Petersen, 1995, Mol. Gen. Genet., 249:425-31), cell surface receptors (Kay, 1993, Gene 128:59-65), and extracellular and intracellular proteins (Gram, 1993, J. Immunol. Methods, 161:169-76).

The concept of using filamentous phages, such as M13 or fd, for displaying peptides on phage capsid surfaces was first introduced by Smith, 1985, Science 228:1315-1317. Peptides have been displayed on phage surfaces to identify many potential ligands (see, e.g., Cwirla, 1990, Proc. Natl. Acad. Sci. USA, 87:6378-6382). There are numerous systems and methods for generating phage display libraries described in the scientific and patent literature, see, e.g., Sambrook and Russell, *Molecule Cloning: A Laboratory Manual,* 3rd edition, Cold Spring Harbor Laboratory Press, Chapter 18, 2001; Phage, *Display of Peptides and Proteins: A Laboratory Manual,* Academic Press, San Diego, 1996; Crameri, 1994, Eur. J. Biochem. 226:53-58; de Kruif, 1995, Proc. Natl. Acad. Sci. USA, 92:3938-42; McGregor, 1996, Mol. Biotechnol., 6:155-162; Jacobsson, 1996, Biotechniques, 20:1070-1076; Jespers, 1996, Gene, 173:179-181; Jacobsson, 1997, Microbiol Res., 152:121-128; Fack, 1997, J. Immunol. Methods, 206:43-52; Rossenu, 1997, J. Protein Chem., 16:499-503; Katz, 1997, Annu. Rev. Biophys. Biomol. Struct., 26:27-45; Rader, 1997, Curr. Opin. Biotechnol., 8:503-508; Griffiths, 1998, Curr. Opin. Biotechnol., 9:102-108.

Typically, exogenous nucleic acids encoding the protein sequences to be displayed are inserted into a coat protein gene, e.g. gene III or gene VIII of the phage. The resultant fusion proteins are displayed on the surface of the capsid. Protein VIII is present in approximately 2700 copies per phage, compared to 3 to 5 copies for protein III (Jacobsson (1996), supra). Multivalent expression vectors, such as phagemids, can be used for manipulation of the nucleic acid sequences encoding the fluorescent binding library and production of phage particles in bacteria (see, e.g., Felici, 1991, J. Mol. Biol., 222:301-310).

Phagemid vectors are often employed for constructing the phage library. These vectors include the origin of DNA replication from the genome of a single-stranded filamentous bacteriophage, e.g., M13 or f1 and require the supply of the other phage proteins to create a phage. This is usually supplied by a helper phage which is less efficient at being packaged into phage particles. A phagemid can be used in the same way as an orthodox plasmid vector, but can also be used to produce filamentous bacteriophage particle that contain single-stranded copies of cloned segments of DNA.

The displayed protein does not need to be a fusion protein. For example, a fluorescent binding ligand may attach to a coat protein by virtue of a non-covalent interaction, e.g., a coiled coil binding interaction, such as jun/fos binding, or a covalent interaction mediated by cysteines (see, e.g., Crameri et al., 1994, Eur. J. Biochem., 226:53-58) with or without additional non-covalent interactions. MorphoSys have described a display system in which one cysteine is put at the C terminus of the scFv or Fab, and another is put at the N terminus of g3p. The two assemble in the periplasm and display occurs without a fusion gene or protein.

The coat protein does not need to be endogenous. For example, DNA binding proteins can be incorporated into the phage/phagemid genome (see, e.g., McGregor & Robins, 2001, Anal. Biochem., 294:108-117). When the sequence recognized by such proteins is also present in the genome, the DNA binding protein becomes incorporated into the phage/phagemid. This can serve as a display vector protein. In some cases it has been shown that incorporation of DNA binding proteins into the phage coat can occur independently of the presence of the recognized DNA signal.

Other phage can also be used. For example, T7 vectors, T4 vector, T2 vectors, or lambda vectors can be employed in which the displayed product on the mature phage particle is released by cell lysis.

Another methodology is selectively infective phage (SIP) technology. which provides for the in vivo selection of interacting protein-ligand pairs. A "selectively infective phage" consists of two independent components. For example, a recombinant filamentous phage particle is made non-infective by replacing its N-terminal domains of gene 3 protein (g3p) with a protein of interest, e.g., an antigen. The nucleic acid encoding the antigen can be inserted such that it will be expressed. The second component is an "adapter" molecule in which the fluorescent ligand is linked to those N-terminal domains of g3p that are missing from the phage particle. Infectivity is restored when the displayed protein (e.g., a fluorescent binding ligand) binds to the antigen. This interaction attaches the missing N-terminal domains of g3p to the phage display particle. Phage propagation becomes strictly dependent on the protein-ligand interaction. See, e.g., Spada, 1997, J. Biol. Chem. 378:445-456; Pedrazzi, 1997, FEBS Lett. 415:289-293; Hennecke, 1998, Protein Eng. 11:405-410.

In addition to phage display libraries, analogous epitope display libraries can also be used. For example, the methods of the invention can also use yeast surface displayed libraries (see, e.g., Boder, 1997, Nat. Biotechnol., 15:553-557 and Feldhaus et al., 2003, Nat. Biotechnol., 21, 163-170), which can be constructed using such vectors as the pYD1 yeast expression vector. Other potential display systems include mammalian display vectors and *E. coli* libraries.

In vitro display library formats known to those of skill in the art can also be used, e.g., ribosome displays libraries and mRNA display libraries. In these in vitro selection technologies, proteins are made using cell-free translation and physically linked to their encoding mRNA after in vitro translation. In typical methodology for generating these libraries, DNA encoding the sequences to be selected are transcribed in vitro and translated in a cell-free system.

In ribosome display libraries (see, e.g., Mattheakis et al., 1994, Proc. Natl. Acad. Sci. USA 91:9022-9026; Hanes & Pluckthrun, 1997, Proc. Natl. Acad. Sci. USA, 94:4937-4942) the link between the mRNA encoding the antibody fragment of the invention and the ligand is the ribosome itself. The DNA construct is designed so that no stop codon is included in the transcribed mRNA. Thus, the translating ribosome stalls at the end of the mRNA and the encoded protein is not released. The encoded protein can fold into its correct structure while attached to the ribosome. The complex of mRNA, ribosome and protein is then directly used for selection against an immobilized target. The mRNA from bound ribosomal complexes is recovered by dissociation of the complexes with EDTA and amplified by RT-PCR.

Method and libraries based on mRNA display technology, also referred to herein as puromycin display, are described, for example in U.S. Pat. Nos. 6,261,804; 6,281,223; 6,207, 446; and 6,214,553. In this technology, a DNA linker attached to puromycin is first fused to the 3' end of mRNA. The protein is then translated in vitro and the ribosome stalls at the RNA-DNA junction. The puromycin, which mimics aminoacyl tRNA, enters the ribosomal A site and accepts the nascent polypeptide. The translated protein is thus covalently linked to its encoding mRNA. The fused molecules can then be purified and screened for binding activity. The nucleic acid sequences encoding ligands with binding activity can then be obtained, for example, using RT-PCR.

Plasmid display systems rely on the fusion of displayed proteins to DNA binding proteins, such as the lac repressor (see, e.g., Gates et al., 1996, J. Mol. Biol., 255:373-386; 1996, Methods Enzymol. 267:171-191). When the lac operator is present in the plasmid as well, the DNA binding protein binds to it and can be co-purified with the plasmid. Libraries can be created linked to the DNA binding protein, and screened upon lysis of the bacteria. The desired plasmid/proteins are rescued by transfection, or amplification.

Methods of screening diversity libraries are well known to those in the art. The libraries are typically screened using an antigen, or molecule of interest, for which it is desirable to select a binding partner. Typically, the antigen is attached to a solid surface or a specific tag, such as biotin. The antigen (or molecule of interest) is incubated with a library of the invention. Those polypeptides that bind to the antigen are then separated from those that do not using any of a number of different methods. These methods involve washing steps, followed by elution steps. Washing can be done, for example, with PBS, or detergent-containing buffers. Elution can be performed with a number of agents, depending on the type of library. For example, an acid, a base, bacteria, or a protease can be used when the library is a phage display library.

To facilitate the identification and isolation of the antigen-bound recombinant single chain antibodies of the invention, the single chain antibody can also be engineered as a fusion protein to include selection markers (e.g., epitope tags). Antibodies reactive with the selection tags present in the fusion proteins or moieties that bind to the labels can then be used to isolate the antigen-single chain antibody complex via the epitope or label. For example, scFv/antigen complexes can be separated from non-complexed display particles using antibodies specific for the antibody selection "tag" e.g., an SV5 antibody specific to an SV5 tag (see Example 1, infra). In libraries that are constructed using a display vector, such as a phage display vector, the selected clones, e.g., phage, are then used to infect bacteria.

Other detection and purification facilitating domains include, e.g., metal chelating peptides such as polyhistidine tracts and histidine-tryptophan modules that allow purification on immobilized metals, protein A domains that allow purification on immobilized immunoglobulin, or the domain utilized in the FLAG® extension/affinity purification system (Immunex Corp, Seattle Wash.). Any epitope with a corresponding high affinity antibody can be used, e.g., a myc tag (see, e.g., Kieke, 1997, Protein Eng. 10:1303-1310), V5 (Invitrogen™), or an E-tag (Pharmacia). See also Maier, 1998, Anal. Biochem. 259:68-73; Muller, 1998, Anal. Biochem. 259:54-61. The inclusion of a cleavable linker sequences such as Factor Xa, tobacco etch virus protease or enterokinase (Invitrogen™, San Diego Calif.) between the purification domain and binding site may be useful to facilitate purification. For example, an expression vector of the invention may include a polypeptide-encoding nucleic acid sequence linked to six histidine residues. A widely used tags is six consecutive histidine residues or 6His tag. These residues bind with high affinity to metal ions immobilized on chelating resins even in the presence of denaturing agents and can be mildly eluted with imidazole. Selection tags can also make the epitope or binding partner (e.g., antibody) detectable or easily isolated by incorporation of, e.g., predetermined polypeptide epitopes recognized by a secondary reporter/binding molecule, e.g., leucine zipper pair sequences; binding sites for secondary antibodies; transcriptional activator polypeptides; and other selection tag binding compositions. See also, e.g., Williams, 1995, Biochemistry, 34:1787-1797.

Once a recombinant sulfotyrosine antibody fragment, such as an scFv, is selected, the nucleic acid encoding it is readily obtained. This sequence may then be expressed using any of a number of systems to obtain the desired quantities of the protein. There are many expression systems for that are well know to those of ordinary skill in the art. (See, e.g., *Gene Expression Systems*, Fernandes and Hoeffler, Eds. Academic Press, 1999; Ausubel, supra). Typically, the polynucleotide encoding the sulfotyrosine antibody or antibody fragment is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included.

Another aspect of the invention relates to polynucleotides encoding the sulfotyrosine antibodies and antibody fragments of the invention, as well as vectors and expression vectors comprising such polynucleotides. The polynucleotides and expression vectors of the invention are useful for the production of the antibodies and antibody fragment of the invention.

Recombinant methods of producing the sulfotyrosine antibodies and sulfotyrosine antibody fragments of the invention are preferred. Sulfotyrosine antibody and antibody fragment encoding polynucleotides may be inserted into vectors capable of directing the expression of the desired antibody product in both prokaryotic and eukaryotic host cells. A number of antibody expression vectors have been described, and methods for generating antibodies and antibody fragments are well known in the art. See, for example, Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition).

In one embodiment, phage display systems are used to select single chain antibodies specific for sulfotyrosine. Once isolated, polynucleotides encoding specific sulfotyrosine scFvs may be cloned into expression vectors designed to express full length immunoglobulins as well as fragments thereof having the same specificity. Briefly, the $V_H$ and $V_L$ genes of the single chain antibody are cloned into an immunoglobulin scaffold (i.e., IgG) vector, expressed, and dimerized in order to 'convert' the single chain into a full antibody. The immunoglobulin scaffold may be selected from any of the five major classes of immunoglobulins (IgA, IgD, IgE, IgG and IgM), and subclasses thereof (i.e., IgG-1). Example 3, infra, describes the generation of a full length, anti-sulfotyrosine IgG using the VH and VL genes of an anti-sulfotyrosine scFv. This antibody, like the scFv, also demonstrates sulfotyrosine specificity (see Example 4, infra). Recombinant sulfotyrosine antibodies which are to be used to detect or isolate tyrosine sulfated proteins may be generated from immunoglobulin scaffolds of any vertebrate origin. Recombinant sulfotyrosine antibodies which are to be used therapeutically or diagnostically in an animal in vivo should be based on an immunoglobulin scaffold that matches the immunoglobulins of the animal.

Methods for the conversion of scFvs into intact immunoglobulin molecules are well known, and include without limitation, the methods and expression vectors described in Persic et al., 1997, *An integrated vector system for the eukaryotic expression of antibodies or their fragments after selection*

*from phage display libraries.* Gene 187: 9-18). See also, WO 94/11523, WO 97/9351, EP 0481790.

A sulfotyrosine antibody of the invention may be modified to increase binding affinity, improve stability, and the like, using standard techniques. For example, substitutions, deletions and insertions of amino acids in the antibody polypeptides may be introduced (see, infra).

Based on the specificity for tyrosine sulfate exhibited by two scFvs and the full length IgG described in the Examples, infra, it is not necessary that the recombinant antibodies of the invention be glycosylated or expressed in eukaryotic cells. Various prokaryotic expression host cells may therefore be useful in the generation of such recombinant sulfotyrosine antibodies and fragments. Bacterial expression systems are preferred, and a wide variety of appropriate expression vectors and methods are know. *E. coli* host cells are preferred.

In bacterial expression systems, the expressed light and heavy chain polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, the antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD.sub.550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et at. (1999) J. Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210. Sufficient disulfide bonds are particularly important for the formation and folding of full length, bivalent antibodies having two heavy chains and two light chains.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease 1, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In a preferred embodiment, *E. coli* strains deficient for proteolytic enzymes and transformed with plasmids overexpressing one or more chaperone proteins are used as host cells in the expression system of the invention. Some of these strains are further described in the Examples section below.

Heavy and light chains may be expressed from a single construct or using multiple constructs (expression vectors). For example, United States patent application of Simmons et al., No. 20050170464, describes a process for producing an immunoglobulin in a prokaryotic host cell, using a "separate cistron" expression vector containing a first promoter-cistron pair for expression of an immunoglobulin light chain and a second promoter-cistron pair for expression of an immunoglobulin heavy chain, whereby expression of the light chain and heavy chain are independently regulated by separate promoters. Each cistron within the expression cassette polynucleotide comprises a translation initiation region (TIR) operably linked to the nucleic acid sequence coding for the light chain or heavy chain of the full length antibody. According to this method, the TIR sequences within the expression vector of the invention are manipulated so to provide different translational strength combinations for light and heavy chains.

When using recombinant techniques, the antibody can be produced intracellularly or in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology, 10: 163-167 (1992) describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulphonyl fluoride (PMSF) may be included in any of the foregoing steps to inhibit proteolysis, and antibiotics may be included to prevent the growth of adventitious contaminants.

In another aspect of the invention, the variable heavy and light chains of recombinant sulfotyrosine antibody fragments may be multimerized (i.e., scFvs may be multimerized) to increase binding affinity, by for example, in vitro biotinylation and avidin capture to isolate tetramers. Various strategies have been developed for preparing scFv as a multimeric derivative. This is intended to lead, in particular, to recombinant antibodies with increased binding avidity. In order to achieve multimerization of the scFv, scFv are prepared as fusion proteins with multimerization domains. The multimerization domains may be, e.g. the CH3 region of an IgG or coiled coil structure (helix structures) such as Leucine-zipper domains. However, there are also strategies in which the interaction between the VH/VL regions of the scFv are used for the multimerization (e.g. di-, tri- and pentabodies). Diabodies are a bivalent homodimeric scFv derivative (Hu et al., 1996, PNAS 16: 5879-5883). The shortening of the linker in an scFv molecule to 5-10 amino acids leads to the formation of homodimers in which an inter-chain VH/NL-superimposition takes place. Diabodies may additionally be stabilized by the incorporation of disulphide bridges. Examples of diabody-antibody proteins may be found in Perisic et al., 1994, Structure 2: 1217-1226. By minibody the skilled person means a bivalent, homodimeric scFv derivative. It consists of a fusion protein which contains the CH3 region of an immunoglobulin, preferably IgG, most preferably IgG1 as the dimerization region which is connected to the scFv via a Hinge region (e.g. also from IgG1) and a Linker region. The disulphide bridges in the Hinge region are mostly formed in higher cells and not in prokaryotes. Examples of minibody-antibody proteins may be found in Hu et al., 1996, Cancer Res. 56: 3055-61. A triabody is a trivalent homotrimeric scFv derivative wherein VH-VL are fused directly without a linker sequence leading to the formation of trimers (see, for example, Kortt et al. 1997 Protein Engineering 10: 423-433).

Suitable host cells for cloning or expressing the polynucleotides in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g. *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for sulfotyrosine antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated sulfotyrosine antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/–DHFR (CHO, Urlaub et al., Proc. Natl. Acad. Sci. USA, 77:4216 (1980), including DG44 (Urlaub et al., Som. Cell and Mol. Gen., 12: 555-566 (1986)) and DP12 cell lines); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 (1982)); MRC 5 cells; FS4 cells; and a human hepatoma line (Hep G2).

Host cells are transformed or transfected with the above-described expression or cloning vectors (or these vectors are otherwise introduced, for example by chemical transfection methods) for sulfotyrosine antibody production and cultured in conventional nutrient media modified as appropriate for inducing promoters, selecting transformants, or amplifying the genes encoding the desired sequences.

The host cells used to produce the sulfotyrosine antibodies of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described, for example, in Ham et al., Meth. Enz. 58:44 (1979); Barnes et al., Anal. Biochem., 102:255 (1980); U.S. Pat. Nos. 4,767,704; 4,657,866; 4,927, 762; 4,560,655; or 5,122,469; WO 1990/03430; WO 1987/ 00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In a preferred embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex® G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the full length antibody to Protein A. The solid phase is then washed to remove contaminants non-specifically bound to the solid phase. Finally the full length antibody is recovered from the solid phase by elution.

Another aspect of the invention relates to antibody variants. Amino acid sequence modification(s) of the sulfotyrosine antibodies and fragments of the invention are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed full length antibodies are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but framework region alterations are also contemplated.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the full length antibody of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

Antibody derivatives are also included in the invention. In this regard, the antibodies and antibody variants of the present invention can be further modified to contain additional non-proteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol., polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and or type of polymers used for derivatization can be determined based on considerations including, but not limited to, the particular properties or functions of the antibody to be improved, whether the antibody derivative will be used in a therapy under defined conditions.

Although standard immunization methods have failed to identify an antibody specific for sulfotyrosine, most probably because host animal immune systems are tolerant of the sulfotyrosine modification, immunization methodologies may nevertheless be useful in isolating sulfotyrosine antibodies. In this regard, appropriate antigens, i.e., sulfotyrosine-containing peptide or protein, may be combined with various adjuvants which may result in the immunized host immune system mounting an antibody response.

It is known that the secretory compartment of the cell contains proteins that are tyrosine sulfated. Thus, it is possible that these tyrosine sulfated proteins capture any sulfotyrosine antibodies expressed by the immune system as they pass through the ER. One potential way of overcoming this limitation is by amplifying the variable genes with antibody-producing cells of the immunized host, cloning the amplified variable genes into antibody expression vectors and expressing the antibodies (or fragments thereby encoded), and testing for sulfotyrosine specific reactivity as described, infra.

Specific reactivity of anti-sulfotyrosine antibodies may be established by a number of well known means, including Western blot, immunoprecipitation, ELISA, and FACS analyses using, as appropriate, tyrosine sulfated proteins, peptides, tyrosine sulfated protein-expressing cells or extracts thereof.

In one embodiment, a pair of tyrosine-containing peptides which are identical except in respect of the sulfation state of the tyrosine(s) therein (i.e., sulfated or not sulfated) may be employed to determine specific reactivity. The invention provides two such peptide pairs, each of which were chemically synthesized and contain a single tyrosine residue (see FIG. 1). Other such peptide pairs may be generated and used for this purpose. The ELISA is the preferred assay format, although other routine immunological assays may also be employed. Although specific reactivity may be determined using a single pair of such peptides, the use of multiple pairs of such peptides, wherein tyrosine-flanking residues differ between the pairs, is preferred. In an additional embodiment, multiple pairs of peptides are generated, such that a number of different amino acid residues immediately flank the tyrosine residue. For example, a fully degenerate set of peptide pairs may include all combinations of tyrosine-flanking residues in the polymer $X_n-Z_1-Y-Z_2-X_n$, where $Z_1+Z_2$ represent all combinations of amino acids, Y is tyrosine, and $X_n$ is any amino acid or polymer of amino acids.

In another embodiment, specific reactivity may be established by using a sulfotyrosine-containing protein. In this embodiment, the sulfotyrosine-containing protein is used as the relevant antigen. Irrelevant antigen is generated by de-sulfating the tyrosine(s) in the sulfotyrosine-containing protein, which may be accomplished by the use of a sulfatase enzyme. Specificity is established where the antibody or antibody fragment being assayed binds at least two times more strongly to the relevant antigen in comparison to the irrelevant antigen.

These sulfotyrosine specific antibodies of the invention are useful for the detection, identification, isolation and purification of proteins containing sulfotyrosine residues.

For example, the antibodies and antibody fragments of the invention will be useful in a wide variety of immunological protein assays and isolation procedures, including without limitation, ELISAs, Western Blots and other immunoblot techniques, immunohistochemical assays, various affinity purification methods, and the like. Accordingly, the invention provides various immunological assays useful for the detection of tyrosine sulfated proteins and for the detection of conditions characterized by the sulfation state of a particular protein or proteins. Such assays generally comprise one or more anti-sulfotyrosine antibodies capable of specifically recognizing and binding a tyrosine sulfated protein, and include various immunological assay formats well known in the art, including but not limited to various types of precipitation, agglutination, complement fixation, radioimmunoassays, enzyme-linked immunosorbent and immunofluorescent assays, enzyme-linked assays, immunohistochemical analysis and the like.

The anti-sulfotyrosine antibodies of the invention may also be used to target therapeutic targets. For example, an anti-sulfotyrosine antibody may be conjugated to a toxin molecule and used to target the toxin to a cell expressing a tyrosine sulfated protein.

The invention is further described by way of the following Examples which illustrate the selection and characterization of anti-sulfotyrosine antibodies using an scFv phage display system. Further details of the experimental work described therein may be found in Kehoe, J. N., *New Tools for Studying Tyrosine Sulfation*, PhD Thesis, Univ. California, Berkeley 2004, the contents of which are incorporated by reference herein.

EXAMPLES

Example 1

Isolation of Sulfotyrosine-Specific Single Chain Antibodies

Libraries of phage-displayed single chain variable fragments (scFvs) containing both natural and unnatural combinations of heavy and light chain variable regions were used to select scFvs recognizing tyrosine sulfate, using an in vivo recombination system for scFv production (Sblaftero and Bradbury, 2000, *Exploiting recombination in single bacteria to make large phage antibody libraries*. Nature Biotechnology 18:75-80). Briefly, a small library of scFv was produced in a phagemid with two non-homologous lox recombination. The small size of this library makes it easy to construct and propagate. When one needs scFvs for a selection, bacteria containing the phagemid library are infected with helper phage, and the resultant virions are used to infect bacteria which constitutively express the Cre recombinase. This infection is done at a high multiplicity of infection, 200 virions per bacterium, to ensure that multiple phage genomes enter each bacterium. The Cre recombinase is then able to shuffle the heavy and light chains of the scFvs in vivo, producing a much larger library of scFvs. After in vivo recombination, the recombinase-expressing bacteria are infected with helper phage and the resultant virions collected. Since these bacteria contained multiple phage genomes, one cannot be sure that the virion's phenotype matches its genotype. A new set of bacteria must be infected at a multiplicity of infection less then one. When these bacteria are infected with helper phage the resultant virions will carry the gene for the scFv they display, and can be used for selections.

Synthetic Peptide Antigens:

The antigens for scFv selection were based on two 17-residue peptides with a tyrosine at the central position and a cysteine at the carboxy terminus (FIG. 1). Peptide one (Pep1) is loosely based on the tyrosine sulfation site of PSGL-1. As the goal was to develop an antibody that binds to every sulfated tyrosine rather than a sulfated tyrosine in a particular sequence context, peptide 2 (Pep2) was also synthesized.

The two peptides were synthesized in sulfated and unsulfated forms (FIG. 1). The non-sulfated peptides were synthesized using standard procedures. HPLC analysis of the crude material showed that there was one major product with few contaminants. The masses of the main products were in close agreement with calculated values (Pep1: 2194.63 calculated, 2195.20 observed; Pep2: 1907.26 calculated, 1906.8 observed).

The tyrosine-sulfated peptides were synthesized manually, with N-hydroxybenzotriazole (HOBT) activated by 2-(1H-benzotriazole-1-yl)-1,1,3,3-tetramethyluronium hexafluorophosphate (HBTU). After cleavage and deprotection of Pep1S, the peptide was purified in the same manner as Pep1 and Pep2. The mass was as expected (2274.48 calculated, 2274.20 observed). HPLC purification of the cleaved and deprotected Pep2S showed a relatively clean reaction, but the main product had the mass of a dimer. To reduce Pep2S to a monomer, the crude product was dissolved in deionized water, a small amount of tris-carboxyethylphosphine (Pierce) was added, and the reaction held at room temperature for seven hours. The peptide was then purified via reversed phase HPLC, and characterized by mass spectrometry (1989.26 calculated, 1988.37 observed).

For use in a selection, a portion of the antigenic peptides were biotinylated using EZ-link PEO iodoacetylbiotin (Pierce). The remainder was coupled to the carrier proteins bovine serum albumin (BSA) or ovalbumin (OVA) using sulfosuccinimidyl 4-(N-maleimidomethyl)cyclohexane-1-carboxylate (sulfo-SMCC, Pierce). These conjugates were named using the peptide number, its sulfation state, and the molecule to which it was bound. For example, Pep1S conjugated to BSA is BSA-1S. Pep2 conjugated to biotin will be referred to as Biotin-2.

Preliminary Selections:

Initial attempts to select a sulfotyrosine-specific scFv from phage-displayed scFvs using antigens which had been adsorbed onto the surface of an immunotube (IM) with a general elution methodology failed. Accordingly, the scFvs were first subjected to two preliminary tests: screening for sv5 expression and screening for binding to the background components of an IM selection. Screening for sv5 expression was performed to eliminate phage with genomic deletions, as phage are known to frequently delete foreign DNA from their genome.[5] The phage that delete the scFv gene are able to reproduce more rapidly than phage with a complete scFv gene, and selections can sometimes be overwhelmed by phage which do not carry a scFv gene.

The scFvs were analyzed for the presence or absence of the sv5 tag incorporated into the library construct using an immunoblot approach. Some 3810 colonies stemming from the initial selection attempt (non-stringent second round output and stringent third round output, in roughly equal proportions from selections against both peptide antigen, see Tables 1 and 2) were selected for this preliminary screen. After overnight growth to saturation, colonies were replicated onto UV-sterilized nitrocellulose, and grown on a fresh plate of 2×YT agar, AmpGlu. After overnight growth, nitrocellulose was transferred to a 2×YT agar plate containing 0.25 mM IPTG to induce expression of the scFvs. The colonies were then lysed, and the nitrocellulose probed with mouse anti-sv5 and goat anti-mouse conjugated to alkaline phosphatase (Dako). Thirty percent of the second round output (non-stringent series) was sv5 positive, while 39% of the third round output (stringent series) was sv5 positive (Table 2). Overall, 34% of the clones were sv5 positive (Table 2).

The sv5 positive scFvs were then tested for binding to a mixture of the carrier proteins BSA and OVA. Using these two proteins as antigens, an ELISA was run with crude scFv preparations, as a means of identifying scFvs which bound to fish gelatin. A majority of the sv5 positive second round output (non-stringent series) did not bind a background component of the assay, while 66% of the third round output (stringent series) was background negative.

Selections Against Sulfotyrosine Peptides:

Those sv5 positive scFvs which did not bind a background component of the ELISA (see above) were tested for binding to BSA-1, BSA-1S, BSA-2, and BSA-2S. Preliminary data indicated that 25 clones bound all four of these antigens. The linker between the peptide antigens and the carrier proteins was the only common structure between all four proteins, and it seems to have served as a very good antigen. Five scFvs bound Pep1 regardless of sulfation state, and 2 bound Pep2 regardless of sulfation state. Two clones appeared to bind Pep1S in a sulfate dependent manner.

Some 960 sv5 positive, background negative scFv clones appeared not to bind to anything used in the selections, and these were re-screened using an alkaline phosphatase reporter system in order to select further anti-sulfotyrosine scFvs. Alkaline phosphatase itself and the substrate, p-nitrophenylphosphate, are both quite stable under the conditions used for ELISAs. Therefore a weak ELISA signal will show linear growth for up to 15 hours with minimal background. The second batch of ELISAs was run in the same fashion, except that the tertiary antibody was a 1:2000 dilution of goat α-mouse conjugated to alkaline phosphatase (Dako).

Seventy-four of these scFvs were background positive with alkaline phosphatase. The remaining scFvs were screened for binding to the sulfated antigens as described above. These screens uncovered an additional seven scFvs which appeared to bind the peptide antigens in a sulfate-dependent manner.

TABLE 1

|  | Selection 1 | Selection 2 | Selection 3 | Elution |
|---|---|---|---|---|
| Strategy 1: stringent | | | | |
| Round 1 | BSA-1S | OVA-1S | Biotin-1S | Trypsin |
| Round 2 | OVA-2S | Biotin-2S | BSA-2S | Trypsin |
| Round 3 | Biotin-1S | BSA-1S | OVA-1S | Trypsin |
| Strategy 2: non-stringent | | | | |
| | Selection 4 | Selection 5 | Selection 6 | |
| Round 1 | BSA-1S | OVA-1S | Biotin-1S | Trypsin |
| Round 2 | OVA-1S | Biotin-1S | BSA-1S | Trypsin |
| Strategy 3: specific elution | | | | |
| | Selection 7 | Selection 8 | Selection 9 | Selection 10 |
| Round 1 | BSA-1S | BSA-2S | OVA-1S | OVA-2S | Ty sulfate |
| Round 2 | OVA-1S | OVA-2S | BSA-1S | BSA-2S | Ty sulfate |
| Strategy 4: solution interaction | | | | |
| | Selection 11 | Selection 12 | Selection 13 | Selection 14 |
| Round 1 | Biotin-1S | Biotin-1S | Biotin-2S | Biotin-2S | Trypsin |
| Round 2 | Biotin-1S | Biotin-2S | Biotin-1S | Biotin-2S | Trypsin |

TABLE 2

| | No. picked | % SV5 soluble | % background negative | Sulfate dependent binding - phage ELISA | Sulfate dependent binding - scFv ELISA |
|---|---|---|---|---|---|
| Strategy 1: stringent | 3810 | 1295 | 855 | 9 | 1 |
| Strategy 2: non-stringent | | | | | |

TABLE 2-continued

| | No. picked | % SV5 soluble | % background negative | Sulfate dependent binding - phage ELISA | Sulfate dependent binding - scFv ELISA |
|---|---|---|---|---|---|
| Strategy 3: specific elution | 573 | 243 | 174 | 24 | 1 |
| Strategy 4: solution interaction | 3528 | 2117 | 1863 | 0 | |

Example 2

Characterization of Sulfotyrosine-Specific scFvs

Identification of Unique scFv Genes:

Genes encoding 33 scFvs specific for tyrosine sulfate (Example 1) were amplified via PCR and digested with BstN I, a restriction site common in antibody variable domains. The resultant DNA fragments were separated on a polyacrylamide gel and visualized with ethidium bromide (see Table 2). These results indicated that 28 of the 33 clones produced a full-length scFv gene, while two appeared to be half the length of a normal scFv gene. All 30 of these clones gave unique restriction patterns upon BstN I digestion.

Expression of Unique scFvs:

The unique scFvs were expressed in *E. coli* and purified using standard procedures (see, Kehoe, 2004, supra).

Binding Analysis Using Peptide Antigens:

Purified scFvs were then analyzed for specific binding to the sulfotyrosine peptide antigens. Briefly, immunosorb plates (Nunc™) were coated with either the sulfated or non-sulfated antigens and ELISAs were conducted using scFv-conditioned media as a primary antibody source. Mouse anti-sv5 served as the secondary antibody and goat anti-mouse conjugated to alkaline phosphatase was the tertiary antibody. All scFvs were tested for their ability to bind BSA-1S and BSA-1, and most scFvs were tested for their ability to bind streptavidin-captured Biotin-2S and Biotin-2.

The results are shown in FIG. 2. Two clones, clones scFv 25 and scFv 31, appear to bind specifically to the sulfated peptide antigens (FIG. 2C).

Figure 3:
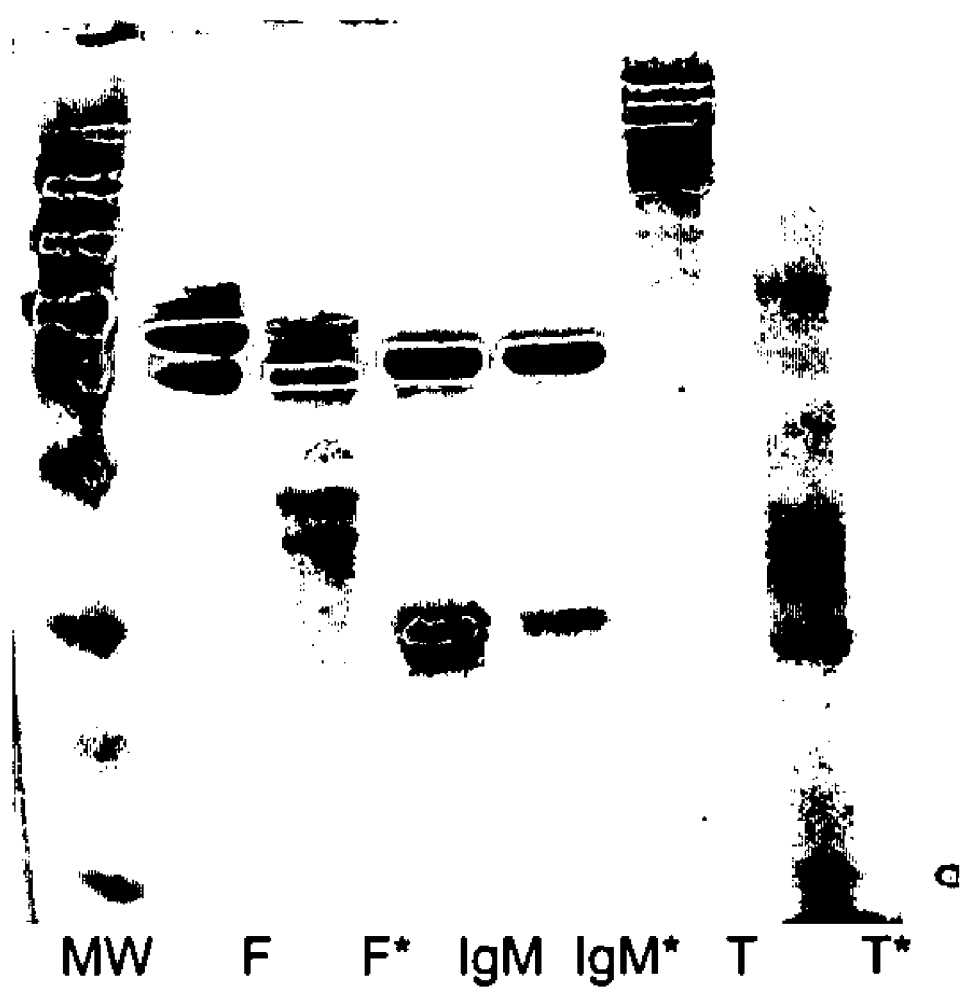
FIG. 3. SDS-PAGE gel (12% Tris-HCl) showing proteins treated and untreated with Abalone sulfatase. 15 µl of native and sulfatase treated (*) fibrinogen, IgM, and thyroglobulin per lane.

Binding Analysis Using Tyrosine-Sulfated Proteins:

The single chain antibody of clone scFv 25 was further analyzed for sulfotyrosine-specific binding using three commercially available tyrosine-sulfated proteins: porcine thyroglobin, rat fibrinogen and mouse IgM (μ specific) (all SIGMA). Abalone sulfatase was used to remove the sulfate modification from the tyrosine residues in these proteins. This sulfatase was found not to degrade the proteins (FIG. 3). An ELISA protocol was used to evaluate scFv 25 binding to each of these proteins, in both their sulfated and de-sulfated states.

Figure 4:
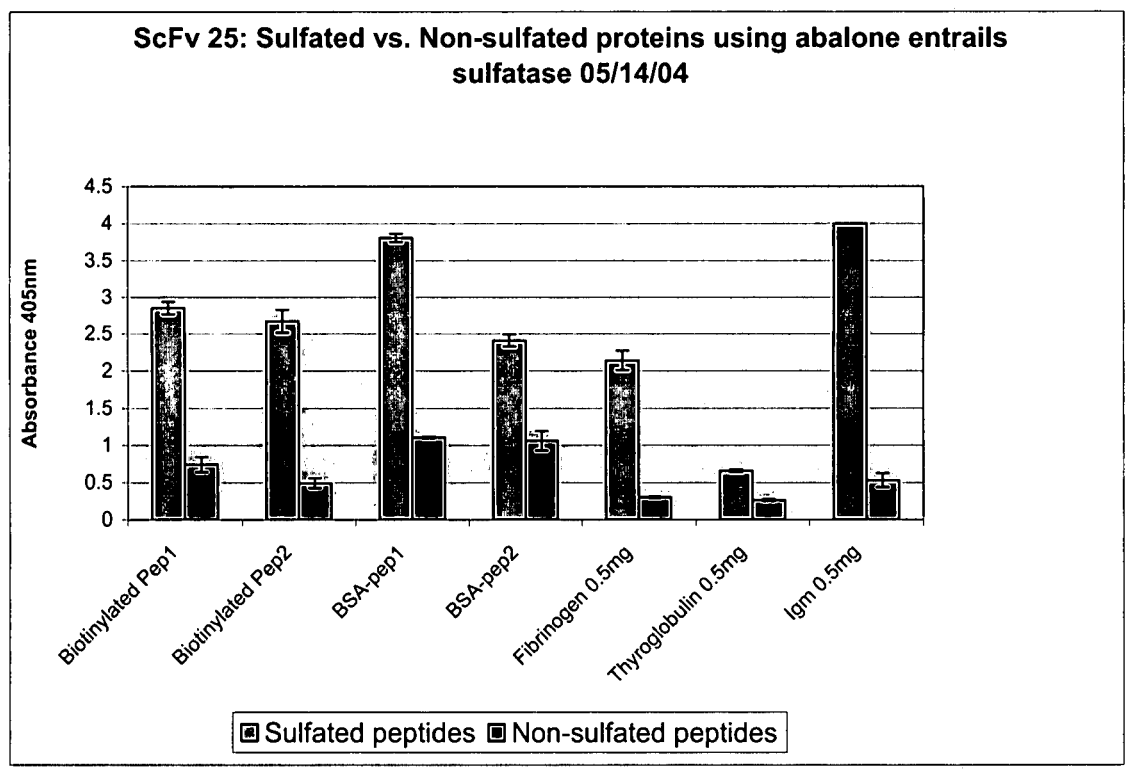
FIG. 4. ELISA results (see Example 2) using scFv 25 against sulfated and unsulfated (Abalone sulfatase digested) proteins and peptides.
Figure 5:
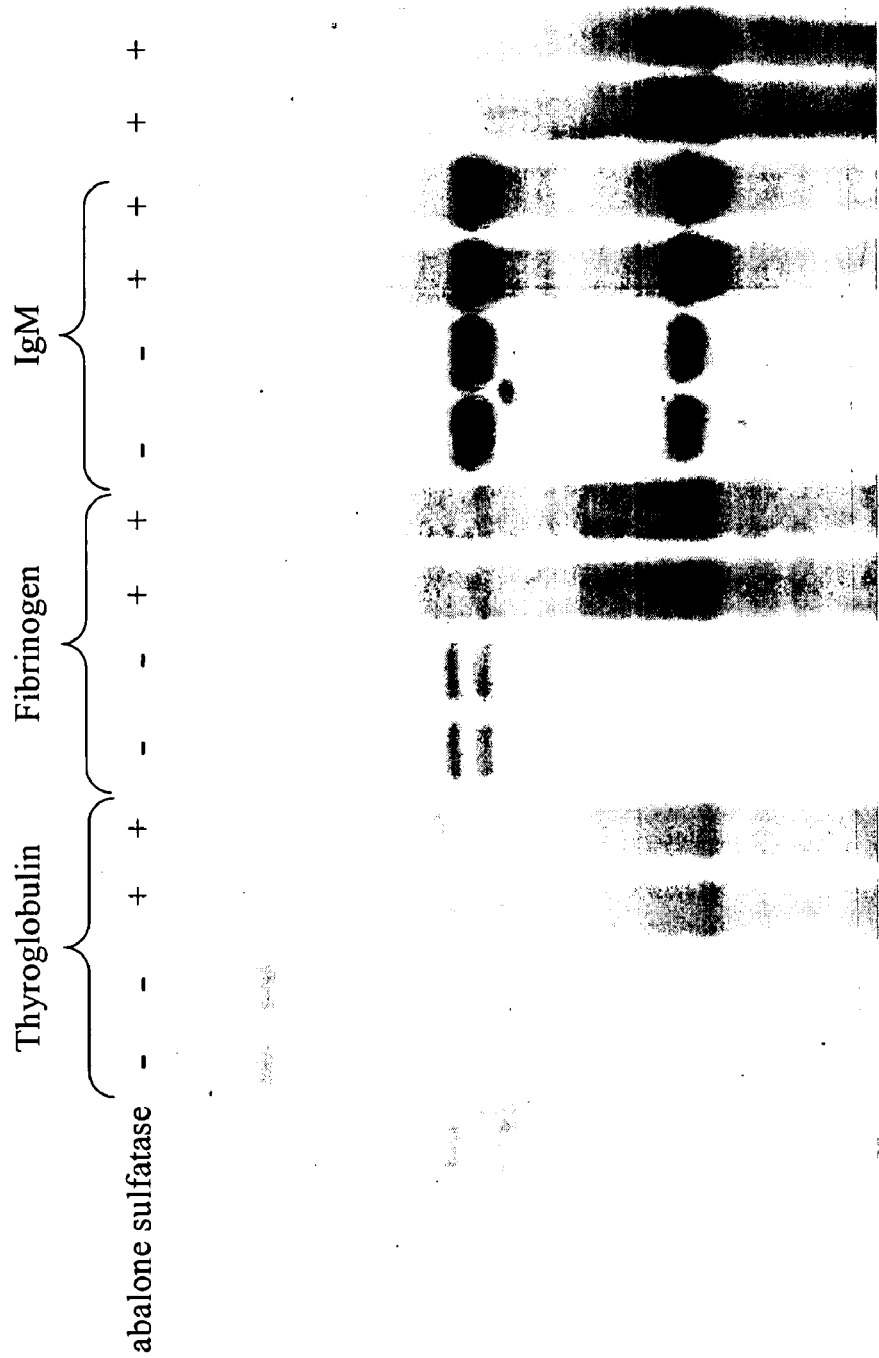
FIG. 5. Polyacrylamide gel electrophoresis of the proteins used in the ELISA (See FIG. 4), showing the effects of sulfatase treatment.

The ELISA results are shown in FIG. 4 and indicate that scFv 25 binds specifically to the sulfated peptides and two of the three sulfated proteins. A polyacrylamide gel electrophoresis of the proteins used in the ELISA is shown in FIG. 5, and indicates the effects of sulfatase treatment.

The nucleotide and translated amino acid sequences of scFv 25, and its component $V_H$ and $V_L$ genes, and Lox linker sequences, are shown in the TABLE OF SEQUENCES, infra.

Example 3

Generation of Anti-Sulfotyrosine IgG

This example describes the construction, expression and purification of an anti-sulfotyrosine IgG using the VH and VK genes of clone scFv 25. Characterization of the resulting complete antibody is described in Example 4.

Materials and Methods

IgG Generation: A full-length, complete IgG anti-sulfotyrosine antibody was generated from scFv 25 as previously described (MacCallum et al., 1996, J. Mol. Biol. 262: 732-745). Briefly, the VH gene was amplified from its scfv expression phagemid clone with the primer pairs 25STVH5'[GTA CCA ACG CGT GTC CAG TCT CAG GTG CAG CTG GTG GAG TCT] [SEQ ID NO: 13] and 25STVH3'[GTC TCC TGA GCT AGC TGA GGA GAC GGT GAC CAG GGT] [SEQ ID NO: 14] by PCR, and the purified DNA fragment was digested with MluI and NheI, ligated into a human IgG1 expression vector N5KG1Val-Lark (a kind gift from Dr. Mitch Reff, IDEC Pharmaceuticals, San Diego) and clones containing the correct VH gene identified by DNA sequencing. The Vk gene of the clone was PCR amplified from the same phagemid vector with the primer pairs 25STVK5' [TAC TCG CAG CAA GCG GTG CAC GAT GTG CAA TTG TGT TGA CAC AGT CTC C] [SEQ ID NO: 15] and 25STVK3' [ATT ATA CGA AGT TAT GGT CGA CCC CGT ACG TTT GAT ATC CAC TTT GGT C] [SEQ ID NO: 16], and cloned into the pCR-2.1 vector (Invitrogen™). Clones containing the correct Vk gene were identified by DNA sequencing. The Vk gene was excised from pCR-2.1 vector with DraIII and BsiWI and ligated into DraIII and BsiWI-digested N5KG1Val-Lark DNA containing the appropriate VH gene. Clones containing the correct VH and Vk gene were identified by DNA sequencing, and vector DNA was used to transfect CHO DG44 cells by electroporation. Stable cell lines were established by selection in G418 and expanded into one liter spinner flasks. Supernatant containing IgG was collected and purified on Protein G column (Pharmacia). The affinity purified IgG was assessed by native and reduced SDS-PAGE, and protein concentration of the final stock was determined by A280 nm.

ELISAs: IgG ELISAs were conducted essentially as described in Example 2, supra, except that 1 μg/well IgG was used and the signal was detected using anti-human AP in 1:2000 dilution (Santa Cruz Biotechnology®).

Tyrosine Sulfate Competition ELISAs: Tyrosine sulfate competition ELISAs were conducted with both IgG and scFv. Bovine fibrinogen IV was biotinylated using the EZ link sulfo NHS LC-LC biotinylation kit (Pierce). 5 μg of biotinylated antigen was incubated with 2 μg of scFv-AP for 1 hr in the presence or absence of competing compounds (tyrosine sulfate, tyrosine phosphate and tyrosine) at 5 mM. After incubation with antibody, the biotinylated antigen with bound scFv-AP was transferred to successive wells using the KingFisher® magnetic particle processor (Thermo Electron). 10 μl of streptavidin coated magnetic beads (Dynal®) were used for each sample and incubated for 10 min. 3×PBST and 3×PBS washes were subsequently carried out and the AP signal after washing detected using the phosphatase substrate kit (Pierce). The ELISA with the IgG was carried out similarly, except that 5 μg of antigen and 1 μg of IgG were used, after the first wash, the complex was incubated with 1:2000 dilution of anti-human AP for 1 hr and washed again prior to measurement. The absorbance at 405 nm reported represents the final value obtained after background subtraction.

Western Blot Analyses: Antigens were separated by polyacrylamide gel electrophoresis using a 4-12% gradient Novex® acrylamide gel (Invitrogen™), and electro-transferred onto nitrocellulose using a semi-wet electroblotter. The antigens were loaded in the following amounts:—E. coli cell extract—30 µg, sulfatase—28 µg, the 3 Fibrinogens—10 µg, C4—0.75 µg and vitronectin 10 µg. Prior to analysis, the blot was blocked using wonder block solution for at least 30 minutes. 200 µg of IgG or 50 µg scFv-AP was diluted in 10 ml of 1×WB and incubated with the transferred blot for 1 hr. The blot was then washed for 10 minutes with PBST (twice) followed by 10 minutes with PBS (twice). The bound IgG was detected using alkaline phosphatase labeled anti-human (Santa Cruz Biotechnology) antibodies after similar washings. Alkaline phosphatase activity was detected using NBT/BCIP (Pierce).

Results

The IgG generated was subjected to characterization using ELISA, competition ELISA and Western Blot.

Figure 6:
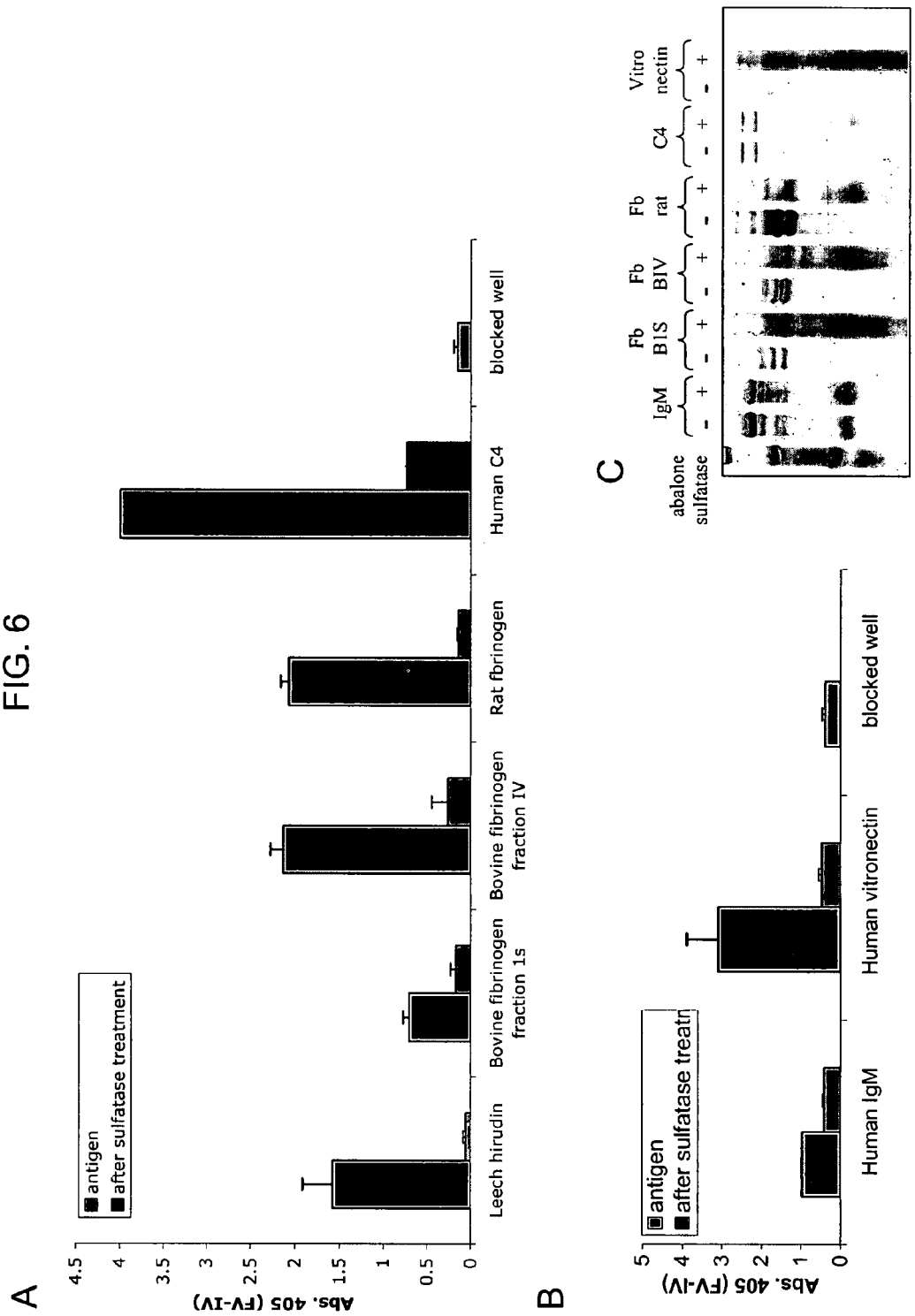
FIG. 6. (A): ELISAs carried out with full length IgG against a number of sulfated proteins. (B): ELISAs carried out with the scFv-AP fusion protein. (C): Polyacrylamide gel electrophoresis of the analyzed proteins before and after sulfatase treatment.

ELISA with the IgG showed that it recognizes hirudin from leeches, three different forms of fibrinogen (fraction 1s—bovine, fibrinogen fraction IV—bovine, fibrinogen-rat) and complement C4 (FIG. 6A), and that the signal was lost upon sulfatase treatment. Interestingly, a correlation between the ELISA signals obtained for the different proteins and the number of sulfated tyrosines was noted: C4 and vitronectin gave the highest ELISA signals and possessed three and two sulfated tyrosines respectively (see FIG. 1D). The scFv-AP conjugate was used to analyze binding to human vitronectin (which could not be tested with the IgG as it gave a strong non-specific signal with the secondary anti-human antibody) and confirm binding to human IgM (FIG. 6B). However, as can be seen from FIG. 6C, with the exception of IgM and C4, there is again significant proteolysis upon sulfatase treatment.

Figure 7:
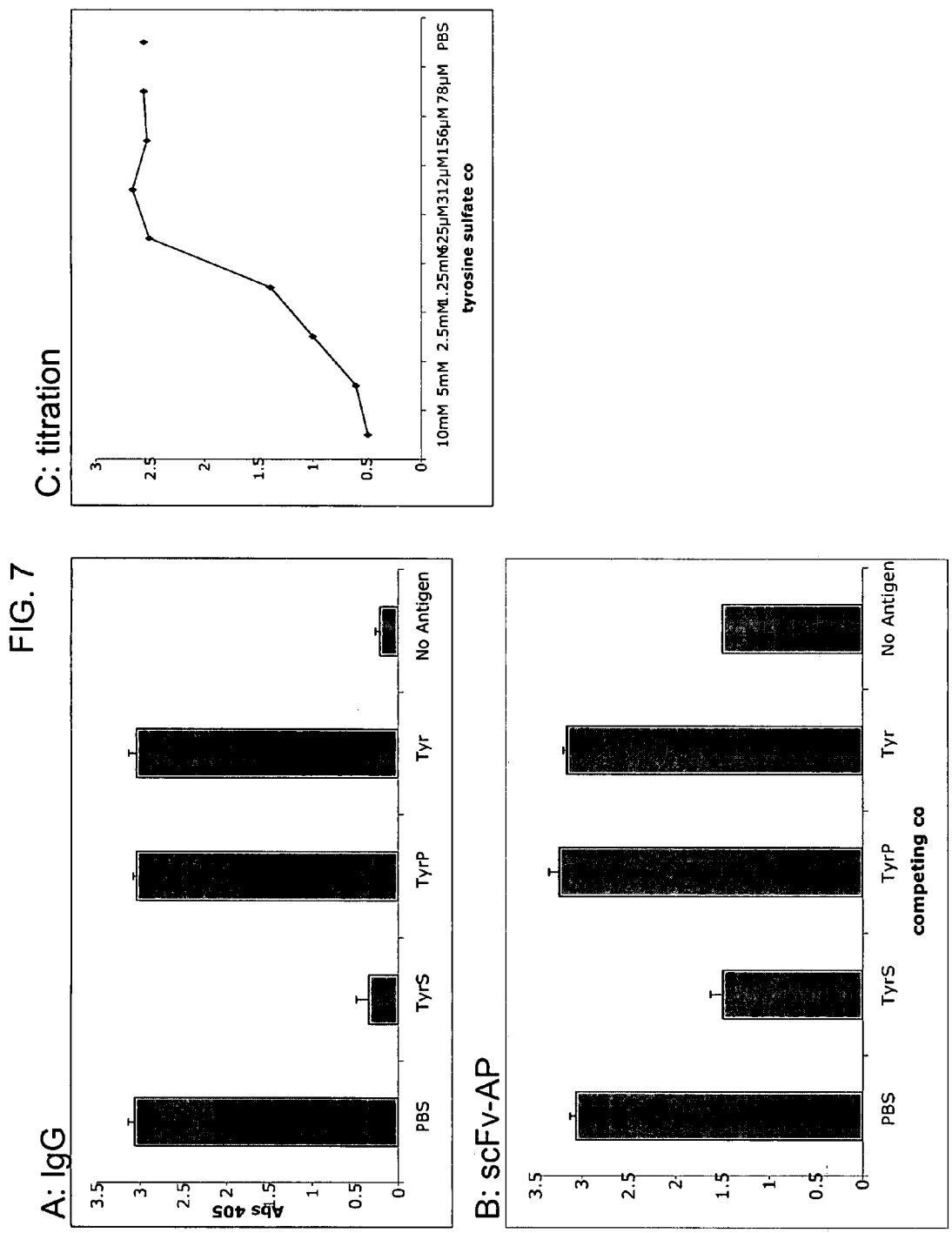
FIG. 7. (A): Inhibition of IgG binding to bovine fibrinogen IV upon incubation with tyrosine sulfate, but not tyrosine or tyrosine phosphate. (B): as A, except the scFv-AP fusion was used. (C): Titration of the inhibition of IgG binding to fibrinogen IV by increasing concentrations of tyrosine sulfate.

In order to further demonstrate the specificity of the antibody for the tyrosine sulfate modification, a magnetic bead based ELISA (KingFisher®, Thermo Electron Inc.) was developed with the goal to see if antibody binding could be inhibited by soluble tyrosine sulfate. Biotinylated bovine fibrinogen IV, the anti-sulfotyrosine antibody and PBS, 5 mM tyrosine sulfate, 5 mM tyrosine phosphate or 5 mM tyrosine were incubated together for an hour. After this period, the amount of antibody which was bound to the biotinylated fibrinogen was assessed by adding streptavidin magnetic beads followed by washing. As can be seen in FIG. 7A, incubation with 5 mM tyrosine sulfate reduced the signal to background levels, while tyrosine phosphate and tyrosine had no effect whatsoever, indicating the specificity of the binding. Similar results were obtained with the scFv-AP fusion (FIG. 7B, and see Example 2), and a control experiment with lysozyme and an anti-lysozyme antibody showed that signal inhibition was not due to non-specific inhibitory effects caused by tyrosine sulfate. This inhibition was further studied by titrating the amount of tyrosine sulfate required to inhibit binding. As can be seen in FIG. 7C, at 10 mM tyrosine sulfate, almost full inhibition is observed, while half maximal inhibition is seen at approximately 1.25 mM.

The question of whether the antibody was able to recognize the tyrosine sulfate modification was also assessed by Western Blot. Analyses with the various fibrinogens and C4 were carried out with the IgG followed by anti-human AP, while the vitronectin was assayed using the scFv-AP conjugate, as it gave a very high background with the secondary antibody. Each of the proteins is clearly recognized by the anti-tyrosine sulfate antibody, with a signal intensity not correlated to the intensity of the coomassie blue band, suggesting that the visible bands are differentially sulfated. These proteins were treated with the abalone sulfatase, modulated to reduce proteolysis for each protein (FIG. 8A). Following sulfatase treatment, the Western blot signal for each protein is abolished or significantly reduced (FIG. 8B), without affecting the integrity of the protein itself. As E. coli does not express any sulfated proteins, lacking the enzymatic machinery to do so (Moore, K. L., 2003, J. Biol. Chem. 278: 24243-24246), the extent of non-specific binding of the antibody was evaluated by probing an overloaded E. coli extract. As can be seen in FIG. 8B, lane 1, no signal is obtained whatsoever, indicating that the antibody is unable to react with the diverse array of E. coli proteins expressed under normal growth conditions.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Table of Sequences

SEQ ID NO: 1 scFv 25 NUCLEOTIDE SEQUENCE [VL-lox linker-VH]

GCAATTGTGTTGACACAGTCTC-
CATCGTCCCTGTCTGCCTCTGTCGGAGACAGAG
TCATCATCACTTGCCGGGCAAGTCAGAG-
TATTACTAAATATGTAAATTGGTATCAG CAAAAAC-
CAGGAAAGGCCCCTAACCTCCTCATC-
TATGGTGCATCCAGTTTGCAAA
GTGGGGTCCCATCAAGGTTCAGTG-
GCAGTGGATCTGGGACAGATTTCACTCTCA CCAT-
CAACAGTCTGCAACCTGAGGACTTTG-
CAACCTACTACTGTCAGCAGACTTA
CAATGTCCCTCGGACGTTCGGCCAAGG-
GACCAAAGTGGATATCAAATCCGGAGG GTCGAC-
CATAACTTCGTATAATGTATACTATAC-
GAAGTTATCCTCGAGCGGTACCC
AGGTGCAGCTGGTGGAGTCTGGGGGAG-
GCTTGGTACAGCCTGGGGGGTCCCTG AGACTCTC-
CTGTGCAGCCTCTGGATTCACCTTTAG-
CAGCTATGCCATGAGCTGGG
TCCGCCAGGCTCCAGGGAAGGGGCTG-
GAGTGGGTCTCAGCTATTAGTGGTAGTG GTGGTAG-
CACATACTACGCAGACTCCGTGAAGGGC-
CGATTCACCATCTCCAGAG
ACAATTCCAAGAACACGCTGTATCT-
TCAAATGAACAGCCTGAGAGCCGAGGACAC GGC-
CGTGTATTACTGTGCGAGATCCACGTAT-
GATAGTAGTGGTTATTACCGGCAC
TGGTACTTCGATCTCTGGGGCCGTG-
GCACCCTGGTCACCGTCTCCTCA

SEQ ID NO: 2 scFv 25 TRANSLATED AMINO ACID SEQUENCE [VL-lox linker-VH]

IVLTQSPSSLSASVGDRVIIT-
CRASQSITKYVNWYQQKPGKAPNLLIY-
GASSLQSGVPS RFSGSGSGTDFTLTINSLQPEDFA-
TYYCQQTYNVPRTFGQGTKVDIKSGGSTITSYNV
YYTKLSSSGTQVQLVESGGGLVQPGGSL-
RLSCAASGFTFSSYAMSWVRQAPGKGL EWV-
SAISGSGGSTYYADSVKGRFTISRDN-
SKNTLYLQMNSLRAEDTAVYYCARSTYD
SSGYYRHWYFDLWGRGTLVTVSS

SEQ ID NO: 3

NUCLEOTIDE SEQUENCE OF VARIABLE LIGHT CHAIN GENE OF scFv 25

GCAATTGTGTTGACACAGTCTC-
CATCGTCCCTGTCTGCCTCTGTCGGAGACAGAG
TCATCATCACTTGCCGGGCAAGTCAGAG-
TATTACTAAATATGTAAATTGGTATCAG CAAAAAC-
CAGGAAAGGCCCCTAACCTCCTCATC-
TATGGTGCATCCAGTTTGCAAA
GTGGGGTCCCATCAAGGTTCAGTG-
GCAGTGGATCTGGGACAGATTTCACTCTCA CCAT-
CAACAGTCTGCAACCTGAGGACTTTG-
CAACCTACTACTGTCAGCAGACTTA
CAATGTCCTCGGACGTTCGGCCAAGG-
GACCAAAGTGGATATCAAA

SEQ ID NO: 4

AMINO ACID SEQUENCE OF VARIABLE LIGHT CHAIN COMPONENT OF scFv 25

IVLTQSPSSLSASVGDRVIIT-
CRASQSITKYVNWYQQKPGKAPNLLIY-
GASSLQSGVPS RFSGSGSGTDFTLTINSLQPEDFA-
TYYCQQTYNVPRTFGQGTKVDIK

SEQ ID NO: 5

NUCLEOTIDE SEQUENCE OF LOX LINKER COMPONENT OF scFv 25

TCCGGAGGGTCGACCATAACTTCG-
TATAATGTATACTATACGAAGTTATCCTCGA GCGG-
TACC

SEQ ID NO: 6

AMINO ACID SEQUENCE OF LOX LINKER COMPONENT OF scFv 25

SGGSTITSYNVYYTKLSSSGT

SEQ ID NO: 7

NUCLEOTIDE SEQUENCE OF VARIABLE HEAVY CHAIN GENE OF scFv 25

CAGGTGCAGCTGGTGGAGTCTGGGGGAG-
GCTTGGTACAGCCTGGGGGGTCCCT GAGACTCTC-
CTGTGCAGCCTCTGGATTCACCTTTAG-
CAGCTATGCCATGAGCTGG
GTCCGCCAGGCTCCAGGGAAGGGGCTG-
GAGTGGGTCTCAGCTATTAGTGGTAGT GGTGGTAG-
CACATACTACGCAGACTCCGTGAAGGGC-
CGATTCACCATCTCCAGA
GACAATTCCAAGAACACGCTGTATCT-
TCAAATGAACAGCCTGAGAGCCGAGGACA CGGC-
CGTGTATTACTGTGCGAGATCCACGTAT-
GATAGTAGTGGTTATTACCGGCA
CTGGTACTTCGATCTCTGGGGCCGTG-
GCACCCTGGTCACCGTCTCCTCA

SEQ ID NO: 8

AMINO ACID SEQUENCE OF VARIABLE HEAVY CHAIN COMPONENT OF scFv 25

QVQLVESGGGLVQPGGSLRLSCAASG-
FTFSSYAMSWVRQAPGKGLEWVSAISGSG GSTYY-
ADSVKGRFTISRDNSKNTLYLQMNSL-
RAEDTAVYYCARSTYDSSGYYRHWY
FDLWGRGTLVTVSS

SEQ ID NO: 9

AMINO ACID SEQUENCE OF SYNTHETIC PEPTIDE Pep1

KDKKYATEYEYLDYDFC

SEQ ID NO: 10

AMINO ACID SEQUENCE OF SYNTHETIC PEPTIDE Pep1S

[asterisk indicates SO3— modification of Tyrosine residue]

KDKKYATEY*EYLDYDFC

SEQ ID NO: 11

AMINO ACID SEQUENCE OF SYNTHETIC PEPTIDE Pep2

KAKISDPDYMTGYMDAC

SEQ ID NO: 12

AMINO ACID SEQUENCE OF SYNTHETIC PEPTIDE Pep2S

[asterisk indicates SO3— modification of Tyrosine residue]

KAKISDPDY*MTGYMDAC

---

What is claimed is:

1. An isolated sulfotyrosine antibody which is specific for a sulfated tyrosine antigenic determinant in a sulfotyrosine-containing polypeptide, and which comprises a heavy chain variable region having the amino acid sequence of SEQ ID NO: 8, and a light chain variable region having the amino acid sequence of SEQ ID NO: 4.

2. The isolated sulfotyrosine antibody of claim 1, which is a full length immunoglobulin selected from the classes consisting of IgA, IgD, IgE, IgG and IgM.

3. An isolated sulfotyrosine antibody fragment of the sulfotyrosine antibody of claim 1 or 2, which is specific for a sulfated tyrosine determinant in a sulfotyrosine containing polypeptide.

4. The isolated sulfotyrosine antibody fragment of claim 3, which is an scFv.

5. The isolated sulfotyrosine antibody fragment of claim 3, which is an Fab or Fab'.

6. The isolated sulfotyrosine antibody of claim 1 or 2, wherein the binding of the antibody to a sulfotyrosine antigen is inhibited by tyrosine sulfate in a competitive immunoassay.

7. The isolated sulfotyrosine antibody of claim 1 or 2, wherein the antibody binds to a sulfotyrosine antigen at least two times more strongly than to an irrelevant antigen or antigen mixture in an ELISA.

8. The isolated sulfotyrosine antibody of claim 1 or 2 which is detectably labeled.

9. The isolated sulfotyrosine antibody of claim 1, which is a recombinant antibody.

10. The isolated sulfotyrosine antibody of claim 2, which is a recombinant antibody.

11. The isolated sulfotyrosine antibody of claim 9 or 10 which is detectably labeled.

12. A composition comprising the sulfotyrosine antibody of any one of claims 1, 2, 9 or 10.

13. A composition comprising the sulfotyrosine antibody of claim 11.

* * * * *

SEQUENCE LISTING

<160> NUMBER OF SEQ ID NOS: 16

<210> SEQ ID NO 1
<211> LENGTH: 759
<212> TYPE: DNA
<213> ORGANISM: Artificial Sequence
<220> FEATURE:
<223> OTHER INFORMATION: Sequence encoding single chain Fv antibody
      clone 25

<400> SEQUENCE: 1

```
gcaattgtgt tgacacagtc tccatcgtcc ctgtctgcct ctgtcggaga cagagtcatc    60
atcacttgcc gggcaagtca gagtattact aaatatgtaa attggtatca gcaaaaacca   120
ggaaaggccc ctaacctcct catctatggt gcatccagtt tgcaaagtgg ggtcccatca   180
aggttcagtg gcagtggatc tgggacagat ttcactctca ccatcaacag tctgcaacct   240
gaggactttg caacctacta ctgtcagcag acttacaatg tccctcggac gttcggccaa   300
gggaccaaag tggatatcaa atccggaggg tcgaccataa cttcgtataa tgtatactat   360
acgaagttat cctcgagcgg tacccaggtg cagctggtgg agtctggggg aggcttggta   420
cagcctgggg gtccctgag actctcctgt gcagcctctg gattcacctt tagcagctat   480
gccatgagct gggtccgcca ggctccaggg aaggggctgg agtgggtctc agctattagt   540
ggtagtggtg gtagcacata ctacgcagac tccgtgaagg gccgattcac catctcccaga  600
gacaattcca agaacacgct gtatcttcaa atgaacagcc tgagagccga ggacacggcc   660
gtgtattact gtgcgagatc cacgtatgat agtagtggtt attaccggca ctggtacttc   720
gatctctggg gccgtggcac cctggtcacc gtctcctca                          759
```

<210> SEQ ID NO 2
<211> LENGTH: 252
<212> TYPE: PRT
<213> ORGANISM: Artificial Sequence
<220> FEATURE:
<223> OTHER INFORMATION: Single chain Fv antibody clone 25

<400> SEQUENCE: 2

```
Ile Val Leu Thr Gln Ser Pro Ser Ser Leu Ser Ala Ser Val Gly Asp
1               5                   10                  15

Arg Val Ile Ile Thr Cys Arg Ala Ser Gln Ser Ile Thr Lys Tyr Val
            20                  25                  30

Asn Trp Tyr Gln Gln Lys Pro Gly Lys Ala Pro Asn Leu Leu Ile Tyr
        35                  40                  45

Gly Ala Ser Ser Leu Gln Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Thr Tyr Asn Val Pro Arg Thr
                85                  90                  95

Phe Gly Gln Gly Thr Lys Val Asp Ile Lys Ser Gly Gly Ser Thr Ile
            100                 105                 110

Thr Ser Tyr Asn Val Tyr Tyr Thr Lys Leu Ser Ser Ser Gly Thr Gln
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Ser Tyr Ala
145                 150                 155                 160

Met Ser Trp Val Arg Gln Ala Pro Gly Lys Gly Leu Glu Trp Val Ser
                165                 170                 175

Ala Ile Ser Gly Ser Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
```

```
                210                 215                 220
Arg Ser Thr Tyr Asp Ser Ser Gly Tyr Tyr Arg His Trp Tyr Phe Asp
225                 230                 235                 240

Leu Trp Gly Arg Gly Thr Leu Val Thr Val Ser Ser
                245                 250

<210> SEQ ID NO 3
<211> LENGTH: 321
<212> TYPE: DNA
<213> ORGANISM: Artificial Sequence
<220> FEATURE:
<223> OTHER INFORMATION: Sequence encoding variable light chain of
      scFv25

<400> SEQUENCE: 3
gcaattgtgt tgacacagtc tccatcgtcc ctgtctgcct ctgtcggaga cagagtcatc     60
atcacttgcc gggcaagtca gagtattact aaatatgtaa attggtatca gcaaaaacca    120
ggaaaggccc ctaacctcct catctatggt gcatccagtt tgcaaagtgg ggtcccatca    180
aggttcagtg gcagtggatc tgggacagat tcactctca ccatcaacag tctgcaacct     240
gaggactttg caacctacta ctgtcagcag acttacaatg tccctcggac gttcggccaa    300
gggaccaaag tggatatcaa a                                              321

<210> SEQ ID NO 4
<211> LENGTH: 106
<212> TYPE: PRT
<213> ORGANISM: Artificial Sequence
<220> FEATURE:
<223> OTHER INFORMATION: Variable light chain of scFv25

<400> SEQUENCE: 4

Ile Val Leu Thr Gln Ser Pro Ser Ser Leu Ser Ala Ser Val Gly Asp
1               5                   10                  15

Arg Val Ile Ile Thr Cys Arg Ala Ser Gln Ser Ile Thr Lys Tyr Val
                20                  25                  30

Asn Trp Tyr Gln Gln Lys Pro Gly Lys Ala Pro Asn Leu Leu Ile Tyr
            35                  40                  45

Gly Ala Ser Ser Leu Gln Ser Gly Val Pro Ser Arg Phe Ser Gly Ser
        50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Thr Tyr Asn Val Pro Arg Thr
                85                  90                  95

Phe Gly Gln Gly Thr Lys Val Asp Ile Lys
            100                 105

<210> SEQ ID NO 5
<211> LENGTH: 63
<212> TYPE: DNA
<213> ORGANISM: Artificial Sequence
<220> FEATURE:
<223> OTHER INFORMATION: Sequence encoding lox linker component of
      scFv25

<400> SEQUENCE: 5
tccggagggt cgaccataac ttcgtataat gtatactata cgaagttatc ctcgagcggt     60
acc                                                                  63

<210> SEQ ID NO 6
```

<211> LENGTH: 21
<212> TYPE: PRT
<213> ORGANISM: Artificial Sequence
<220> FEATURE:
<223> OTHER INFORMATION: lox linker component of scFv25

<400> SEQUENCE: 6

Ser Gly Gly Ser Thr Ile Thr Ser Tyr Asn Val Tyr Tyr Thr Lys Leu
1               5                   10                  15
Ser Ser Ser Gly Thr
            20

<210> SEQ ID NO 7
<211> LENGTH: 375
<212> TYPE: DNA
<213> ORGANISM: Artificial Sequence
<220> FEATURE:
<223> OTHER INFORMATION: Sequence encoding variable heavy chain of
      scFv25

<400> SEQUENCE: 7
caggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg attcaccatc tccagagaca attccaagaa cacgctgtat     240
cttcaaatga acagcctgag agccgaggac acggccgtgt attactgtgc gagatccacg     300
tatgatagta gtggttatta ccggcactgg tacttcgatc tctggggccg tggcaccctg     360
gtcaccgtct cctca                                                      375

<210> SEQ ID NO 8
<211> LENGTH: 125
<212> TYPE: PRT
<213> ORGANISM: Artificial Sequence
<220> FEATURE:
<223> OTHER INFORMATION: Variable heavy chain of scFv25

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Asp Ser Ser Gly Tyr Tyr Arg His Trp Tyr Phe
            100                 105                 110

Asp Leu Trp Gly Arg Gly Thr Leu Val Thr Val Ser Ser
        115                 120                 125

<210> SEQ ID NO 9
<211> LENGTH: 17
<212> TYPE: PRT
<213> ORGANISM: Artificial Sequence
<220> FEATURE:

<223> OTHER INFORMATION: Synthetic peptide

<400> SEQUENCE: 9

Lys Asp Lys Lys Tyr Ala Thr Glu Tyr Glu Tyr Leu Asp Tyr Asp Phe
1               5                   10                  15
Cys

<210> SEQ ID NO 10
<211> LENGTH: 17
<212> TYPE: PRT
<213> ORGANISM: Artificial Sequenct
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa indicates sulfated (SO3-) Tyrosine residue

<400> SEQUENCE: 10

Lys Asp Lys Lys Tyr Ala Thr Glu Xaa Glu Tyr Leu Asp Tyr Asp Phe
1               5                   10                  15
Cys

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Lys Ala Lys Ile Ser Asp Pro Asp Tyr Met Thr Gly Tyr Met Asp Ala
1               5                   10                  15
Cys

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa indicates sulfated (SO3-) Tyrosine residue

<400> SEQUENCE: 12

Lys Ala Lys Ile Ser Asp Pro Asp Xaa Met Thr Gly Tyr Met Asp Ala
1               5                   10                  15
Cys

<210> SEQ ID NO 13
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 13
gtaccaacgc gtgtccagtc tcaggtgcag ctggtggagt ct                        42

<210> SEQ ID NO 14
<211> LENGTH: 36
<212> TYPE: DNA
<213> ORGANISM: Artificial Sequence

```
<220> FEATURE:
<223> OTHER INFORMATION: Synthetic oligonucleotide primer

<400> SEQUENCE: 14
gtctcctgag ctagctgagg agacggtgac cagggt                              36

<210> SEQ ID NO 15
<211> LENGTH: 49
<212> TYPE: DNA
<213> ORGANISM: Artificial Sequence
<220> FEATURE:
<223> OTHER INFORMATION: Synthetic oligonucleotide primer

<400> SEQUENCE: 15
tactcgcagc aagcggtgca cgatgtgcaa ttgtgttgac acagtctcc                49

<210> SEQ ID NO 16
<211> LENGTH: 49
<212> TYPE: DNA
<213> ORGANISM: Artificial Sequence
<220> FEATURE:
<223> OTHER INFORMATION: Synthetic oligonucleotide primer

<400> SEQUENCE: 16
attatacgaa gttatggtcg accccgtacg tttgatatcc actttggtc                49
```